United States Patent [19]

Cook et al.

[11] Patent Number: 5,717,083
[45] Date of Patent: Feb. 10, 1998

[54] PHOSPHORAMIDATE AND PHOSPHOROTHIOMIDATE OLIGOMERIC COMPOUNDS

[75] Inventors: Phillip Dan Cook, Vista; Oscar Acevedo, San Diego; Normand Hebert, Cardiff, all of Calif.

[73] Assignee: ISIS Pharmaceuticals, Inc., Carlsbad, Calif.

[21] Appl. No.: 693,112

[22] PCT Filed: Feb. 23, 1995

[86] PCT No.: PCT/US95/02267

§ 371 Date: Aug. 19, 1996

§ 102(e) Date: Aug. 19, 1996

[87] PCT Pub. No.: WO95/23160

PCT Pub. Date: Aug. 31, 1995

Related U.S. Application Data

[63] Continuation-in-part of Ser. No. 200,638, Feb. 23, 1994, Pat. No. 5,637,684.

[51] Int. Cl.$^6$ .................. C07H 21/00; C07D 239/00
[52] U.S. Cl. .................. 536/23.1; 536/24.5; 544/242; 544/264; 568/8; 568/11; 568/36
[58] Field of Search .................. 536/23.1, 24.1, 536/24.3, 24.5, 25.3; 544/242, 264; 568/8, 11, 36

[56] References Cited

U.S. PATENT DOCUMENTS

| | | | |
|---|---|---|---|
| 3,687,808 | 8/1972 | Merigan, Jr. et al. | 435/91.3 |
| 4,547,569 | 10/1985 | Letsinger et al. | 536/25.32 |
| 4,958,013 | 9/1990 | Letsinger | 536/24.5 |
| 5,218,103 | 6/1993 | Caruthers et al. | 536/25.33 |
| 5,272,250 | 12/1993 | Spielvogel et al. | 530/300 |
| 5,362,899 | 11/1994 | Campbell | 558/108 |
| 5,578,718 | 11/1996 | Cook et al. | 536/27.21 |
| 5,587,471 | 12/1996 | Cook et al. | 536/25.3 |

FOREIGN PATENT DOCUMENTS

| | | |
|---|---|---|
| 0 219 342 A2 | 4/1987 | European Pat. Off. |
| WO 91/19735 | 12/1991 | WIPO . |
| WO 93/04204 | 3/1993 | WIPO . |
| WO 93/07883 | 4/1993 | WIPO . |

OTHER PUBLICATIONS

Agrawal et al., "Oligodeoxynucleoside Phosphoramidates and Phosphorothioates as Inhibitors of Human Immunodeficiency Virus", *Proc. Natl. Acad. Sci.* 1988, 85, 7079–7083.

Chu et al., "Derivatization of Unprotected Polynucleotides" *Nucleic Acids Research*, 1983, 11, 6513–6529.

Dagle et al., "Targeted Degradation of mRNA in Xenopus Oocytes and Embryos Directed by Modified Olignucleotides: Studies of An2 and Cyclic in Embryogenesis", *Nucleic Acids Research*, 1990, 18, 4751–4757.

Ecker et al., "Rational Screening of Oligonucleotide Combinatorial Libraries for Drug Discovery", *Nucleic Acids Research*, 1993, 21, 1853–1856.

Eritja et al., "O–Aryl Phosphoramidites: Synthesis, Reactivity and Evaluation of Their Use for Solid–Phase Synthesis of Oligonucleotides", *Tetrahedron*, 1990, 45, 721–730.

Froehler et al., "Phosphoramidate analogues of DNA: Synthesis and Thermal Stability of Heteroduplexes", *Nucleic Acids Research*, 1988, 16, 4831–4839.

Houghten et al., "Generation and use of synthetic peptide combinatorial libraries for basic research and drug discovery", *Nature*, 1991, 354, 84–86.

Jäger et al., "Oligonucleotide N–Alkylphosphoramidates: Synthesis and Binding to Polynucleotides", *Biochemistry*, 1988, 27, 7237–7246.

Letsinger et al., "Cholesteryl–Conjugated Oligonucleotides: Synthesis, Properties, and Activity as Inhibitors of Replication of Human Immunodeficiency Virus in Cell Culture", *Proc. Natl. Acad. Sci.*, 1989, 86, 6553–6556.

Ohtsuka et al., New phosphoramidates as protecting groups in ribooligonucleotides synthesis *Nucleic Acids Research*, 1976, 3, 653–660.

Wyatt et al., "Combinatorially Selected Guanosine–Quartet Structure is a Potent Inhibitor of Human Immunodeficiency Virus Envelope–Mediated Cell Fusion", *Proc. Natl. Acad. Sci. USA*, 1994, 91, 1356–1360.

Zhou et al., "Synthesis and Antitumor Activity of Polyphosphates Containing both Nitrogen Mustard and Ipophilic Groups", 1989, 10(9), 935–938.

Achari, "Facing up to Membranes: Struture/Function Relationships in Phospholipases", *Cold Spring Harbor Symp. Quant. Biol.*, 1987, 52, 441–452.

Alul et al., "Oxalyl–CPG: a labile support for synthesis of sensitive oligonucleotides derivatives", *Nucl. Acids Res.*, 1991, 19(7), 1527–1532.

(List continued on next page.)

*Primary Examiner*—David Guzo
*Attorney, Agent, or Firm*—Woodcock Washburn Kurtz Mackiewicz & Norris LLP

[57] ABSTRACT

Compounds are provided having structure (I), wherein the L groups are backbone segments, the Y and T groups are functional groups for interacting with target molecules of interest, the X groups are oxygen or sulfur and the E groups are H, conjugate groups or intermediate groups used during the synthesis of the compounds and wherein the compounds are prepared using H phosphonate type chemistry wherein the functional groups are added during an oxidation step or during a coupling step.

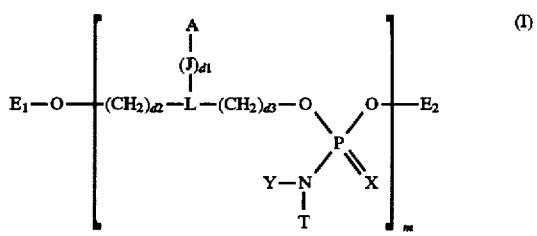

40 Claims, No Drawings

OTHER PUBLICATIONS

Beaucage et al., "Advances in the Synthesis of Oligonucleotides by the Phosphoramidite Approach", *Tetra. Lett.*, 1992, 48(12), 2223–2311.

Bomalaski et al., "Human Extracellular Recombinant Phospholipase $A_2$ Induces an Inflammatory Response in Rabbit Joints", *J. Immunol.*, 1991, 146(11), 3904–3910.

Brückner et al., "Automated Enantioseparation of Amino Acids by Derivatization with o-Phthaldialdehyde and N-Acylated Cysteins", *J. Chrom.*, 1989, 476, 73–82.

Burack et al., "Role of Lateral Phase Separation in the Modulation of Phospholipase $A_2$ Activity", *Biochem.*, 1993, 32, 583–589.

Campbell et al., "Inhibition of Phospholipase $A_2$; a Molecular Recognition Study", *J. Chem. Soc., Chem. Commun.*, 1988, 1560–1562.

Cho et al., "The Chemical Basis for Interfacial Activation of Monomeric Phospholipases $A_2$", *J. Biol. Chem.*, 1986, 263(23), 11237–11241.

Concise Encyclopedia of Polymer Science and Engineering, "Polynucleotides", Kroschwitz, J.I. (ed.), John Wiley & Sons, 1990, 858–859.

Damha et al., "An improved procedure for derivatization of controlled-pore glass beads for solid-phase oligonucleotide synthesis", *Nucl. Acids Res.*, 1990, 18(13), 3813–3821.

Davidson et al., "Inhibition of Phospholipase $A_2$ by Lipocortins and Calpactins", *J. Biol. Chem.*, 1987, 262(4), 1698–1705.

Davidson et al., "1-Stearyl,2-Stearoylaminodeoxy Phosphatidylcholine, A Potent Reversible Inhibitor of Phospholipase $A_2$", *Biochem. Biophys. Res. Commun.*, 1986, 137(2), 587–592.

Dennis, "Phospholipases", *The Enzymes*, Boyer, P.D. (ed.), Academic Press, New York, 1983, vol. 16, 307–353.

Englisch et al, "Chemically Modified Oligonucleotides as Probes and Inhibitors", *Angew. Chem. Int. Ed. Engl.*, 1991, 30(6), 613–629.

Farooqui et al., "Effect of Structural Variations in Cholesteryl-Conjugated Oligonucleotides on Inhibitory Activity toward HIV-1", *Bioconj. Chem.*, 1991, 2, 422–426.

Franson et al., "Phospholipid metabolism by phagocytic cells. Phospholipases $A_2$ associated with rabbit polymorphonuclear leukocyte granules", *J. Lipid Res.*, 1974, 15, 380–388.

Froehler et al., "Nucleoside H-Phosphonates: Valuable Intermediates in the Synthesis of Deoxyoligonucleotides", *Tetra. Lett.*, 1986, 27(4), 469–472.

Froehler et al., "Deoxynucleoside H-Phosphonate Diester Intermediates in the Synthesis of Internucleotide Phosphate Analogues", *Tetra. Lett.*, 1986, 27(46), 5575–5578.

Garegg et al., "Nucleoside Hydrogenphosphonates in Oligonucleotide Synthesis", *Chem. Scripta*, 1986, 26, 159–162.

Geysen et al., "Strategies for epitope analysis using peptide synthesis", *J. Immunol. Meth.*, 1987, 102, 259–274.

Glaser et al., "Phospholipase $A_2$ enzymes: regulation and inhibition", *TiPs*, 1993, 14, 92–98.

Grainger et al., "An enzyme caught in action: direct imaging of hydrolytic function and domain formation of phospholipase $A_2$ in phosphatidylcholine monolayers", *FEBS Lett.*, 1989, 252(1,2), 73–82.

Gryaznov et al., "A New Approach to the Synthesis of Oligodeoxyribonucleotides with Alkylamino Groups Linked to Internucleotide Phosphate Groups", *Tetra. Lett.*, 1991, 32(30), 3715–3718.

Gryaznov et al., "A New Method for the Synthesis of Oligodeoxyribonucleotides Containing Internucleotide Phosphoramidate Bonds", *Tetra. Lett.*, 1990, 31(22), 3205–3208.

Iso et al., "Synthesis of Viologen-Tagged Oligodeoxynucleotides", *Tetra. Lett.*, 1992, 33(4), 503–506.

Jung et al., "Hybridization of Alternating Cationic/Anionic Oligonucleotides to RNA Segments", *Nucleosides & Nucleotides*, 1994, 13(6&7), 1597–1605.

Letsinger et al., "Cationic Oligonucleotides", *J. Am. Chem. Soc.*, 1988, 110, 4470–4471.

Lombardo et al., "Cobra Venom Phospholipase $A_2$ Inhibition by Manoalide", *J. Biol. Chem.*, 1985, 260(12), 7234–7240.

Marki et al., "Differential inhibition of human secretory and cytosolic phospholipase $A_2$", *Agents Actions*, 1993, 38, 202–211.

Miyake et al., "The Novel Natural Product YM-26567-1 [(+)-trans-4-(3-dodecanoyl-2,4,6-trihydroxyphenyl)-7-hydroxy-2-(4-hydroxyphenyl)chroman]: A Competitive Inhibitor of Group II Phospholipase A2", *J. Pharm. Exp. Therap.*, 1992, 263(3), 1302–1307.

Noel et al., "Phospholipase A2 Engineering. 3. Replacement of Lysine-56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

*Nucleic Acids in Chemistry and Biology*, "Chemical Synthesis", Blackburn, G.M. and Gait, M.J. (eds.), IRL Press at Oxford University Press: New York, 1990, Ch. 3, 73–133.

Ohlmeyer et al., "Complex synthetic chemical libraries indexed with molecular tags", *Proc. Natl. Acad. Sci. USA*, 1993, 90, 10922–10926.

Oinuma et al., "Synthesis and Biological Evaluation of Substituted Benzenesulfonamides as Novel Potent Membrane-Bound Phospholipase $A_2$ Inhibitors", *J. Med. Chem.*, 1991, 34, 2260–2267.

Owens et al., "The Rapid Identification of HIV Protease Inhibitors Through the Synthesis and Screening of Defined Peptide Mixtures", *Biochem. Biophys. Res. Commun.*, 1991, 181(1), 402–408.

Pon, R.T., Protocols for Oligonucleotides and Analogs: Synthesis and Properties, Agrawal, S. (ed.), Humana Press, Totowa, NJ, 1993, 465–496.

Pruzanski et al., "Enzymatic Activity and Immunoreactivity of Extracellular Phospholipase A2 in Inflammatory Synovial Fluids", *Inflamm.*, 1992, 16(5), 451–457.

Scott et al., "Interfacial Catalysis: The Mechanism of Phospholipase $A_2$", *Science*, 1990, 250, 1541–1546.

Simon et al., "Peptoids: A modular approach to drug discovery", *Proc. Natl. Acad. Sci. USA*, 1992, 89, 9367–9371.

Tanaka et al., "A Novel Type of Phospholipase A2 Inhibitor, Thielocin A1β, and Mechanism of Action", *J. Antibiotics*, 1992, 45(7), 1071–1078.

Vishwanath et al., "Edema-Inducing Activity of Phospholipase $A_2$ Purified from Human Synovial Fluid and Inhibition by Aristolochic Acid", *Inflamm.*, 1988, 12(6), 549–561.

Washburn et al., "Suicide-inhibitory Bifunctionally Linked Substrates (Siblinks) as Phospholipase $A_2$ Inhibitors", *J. Biol. Chem.*, 1991, 266(8), 5042–4048.

Wery et al., "Structure of recombinant human rheumatoid arthritic synovial fluid phospholipase $A_2$ at 2.2 Å resolution", *Nature*, 1991, 352, 79–82.

Wright et al., "Large Scale Synthesis of Oligonucleotides via Phosphoramidite Nucleosides and a High–loaded Polystyrene Support", *Tetra. Lett.*, 1993, 34(21), 3373–3376.

Wu et al., "Purification and Sequence Analysis of Synthetic Oligodeoxyribonucleotides", *Oligonucleotide Synthesis: a practical approach*, Gait, M.J. (ed.), IRL Press at Oxford University Press: New York, 1990.

Yang et al., "Studies on the status of lysine residues in phospholipase $A_2$ from *Naja naja atra* (Taiwan cobra) snake venom", *Biochem. J.*, 1989, 262, 855–860.

Yuan et al., "Synthesis and Evaluation of Phospholipid Analogues as Inhibitors of Cobra Venom Phospholipase $A_2$", *J. Am. Chem. Soc.*, 1987, 109, 8071–8081.

Zuckerman et al., "Efficient Method for the Preparation of Peptoids [Oligo(N–substituted glycines)] by Submonomer Solid–Phase Synthesis", *J. Am. Chem. Soc.*, 1992, 114, 10646–10647.

PHOSPHORAMIDATE AND PHOSPHOROTHIOMIDATE OLIGOMERIC COMPOUNDS

CROSS REFERENCE TO RELATED APPLICATIONS

This application is a 371 application of PCT/US95/02267, filed Feb. 23, 1995 and is a continuation-in-part of U.S. application Ser. No. 08/200,638, filed Feb. 23, 1994, now U.S. Pat. No. 5,637,684. The contents of the foregoing patent application are incorporated herein by reference.

FIELD OF THE INVENTION

This invention is directed to oligomeric compounds comprising monomeric units having a backbone segment covalently bound to a phosphoramidate or phosphorothioamidate moiety. Functional groups are attached independently either at the backbone segment, at the phosphoramidate or phosphorothioamidate moieties or both. Substitutions can be effected through an optional tether group. The oligomers are synthesized having either a random or a predefined sequences of units. Randomization can be effected independently at the backbone segment, or at the phosphoramidate or phosphorothioamidate moieties, via the covalent bonding of diverse functional groups. The functional group or groups on the monomeric units can, inter alia, provide for binding of the oligomeric structures to proteins, nucleic acids, lipids and to other biological targets. In preferred embodiments, the compounds of the invention act as inhibitors of enzymes such as phospholipase $A_2$: as inhibitors of pathogens such as virus, mycobacterium, bacteria (gram negative and gram positive), protozoa and parasites; as inhibitors of ligand-receptor interactions such as PDGF (platelet derived growth factor), LTB4 (leukotriene B4), IL-6 and complement $C5_A$; as inhibitors of protein/protein interactions including transcription factors such as p50 ($NF_{kappa}B$ protein) and fos/jun; and for the inhibition of cell-based interactions including ICAM induction (using inducers such as IL1-β, TNF and LPS). In other preferred embodiments, the compounds of the invention are used as diagnostic reagents, including diagnostic reagents in the tests for each of the above noted systems, and as reagents in assays and as probes.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the other hand, laboratory syntheses give unambiguous products, but the preparation of each new structure requires significant amounts of resources. Generally, the de novo design of active compounds based on the high resolution structures of enzymes has not been successful.

In order to maximize the advantages of each classical approach, new strategies for combinatorial unrandomization have been developed independently by several groups. Selection techniques have been used with libraries of peptides (see Geysen, H. M., Rodda, S. J., Mason, T. J., Tribbick, G. & Schoofs, P. G., *J. Immun. Meth.* 1987, 102, 259–274; Houghten, R. A., Pinilla, C., Blondelle, S. E., Appel, J. R., Dooley, C. T. & Cuervo, J. H., *Nature*, 1991, 354, 84–86; Owens, R. A., Gesellchen, P. D., Houchins, B. J. & DiMarchi, R. D., *Biochem. Biophys. Res. Commun.*, 1991, 181, 402–408), nucleic acids (see Wyatt, J. R., et al., *Proc. Natl. Acad. Sci. U.S.A.*, (in press); Ecker, D. J., Vickers, T. A., Hanecak, R., Driver, V. & Anderson, K., *Nucleic Acids Res.*, 1993, 21, 1853–1856) and nonpeptides (see Simon, R. J., et al., *Proc. Natl. Acad. Sci. U.S.A.*, 1992, 89, 9367–9371; Zuckermann, R. N., et al., *J. Amer. Chem. Soc.*, 1992, 114, 10646–10647; Bartlett, Santi, Simon, PCT WO91/19735; and Ohlmeyer, M. H., et al., *Proc. Natl. Acad. Sci. U.S.A.*, 1993, 90, 10922–10926). The techniques involve iterative synthesis and screening of increasingly simplified subsets of oligomers. Monomers or submonomers that have been utilized include amino acids and nucleotides both of which are bi-functional. Utilizing these techniques, libraries have been assayed for activity in either cell-based assays, or for binding or inhibition of purified protein targets.

A technique, called SURF (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g. NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the assay can be identified. The SURF technique is described in Ecker, D. J., Vickers, T. A., Hanecak, R., Driver, V. & Anderson, K., *Nucleic Acids Res.*, 1993, 21, 1853–1856. The SURF method is further described in PCT patent application WO 93/04204, the entire disclosure of which is herein incorporated by reference.

Phosphoramidates were noted for use as protecting groups for ribooligonucleotide synthesis by Ohtsuka, E., et. al., *Nucleic Acids Research*, 1976, 3, 653. Oligonucleotides having a phosphoramidate linked amino group at their 5' end were disclosed by Chu, B. C. F., et. al., *Nucleic Acids Research*, 1983, 11, 6513. Oligodeoxynucleotides (DNA) containing internucleotide phosphoramidate linkages have been synthesized by several groups. However, in each such synthesis, the phosphoramidate linkage has only been utilized to connect adjacent nucleosides, i.e. an internucleotide linkage. One of these synthesis was reported by Froehler, B., et. al., *Nucleic Acids Research*, 1988, 16, 4831–4838. As reported by Froehler, et. al., the stability of duplexes ranging from dimers to fifteen mers was studied to determine the ability of the oligonucleotides to hybridize to complementary diester oligonucleotides. Thermal denaturation revealed enhanced stability for dimers and trimers but less stability for longer sequences. Other phosphoramidite containing oligonucleotides are disclosed by Eritja, R. et. al., *Tetrahedron*, 1990, 45, 721; and Jager, A., et. al., *Biochemistry*, 1988, 27, 7237.

In U.S. Pat. No. 5,272,250, issued Dec. 21, 1993, boronated phosphoramidate compounds are disclosed. The disclosed compounds include a boron moiety connected through a tether to the nitrogen of the phosphoramidate. The boronated compound is present as either a monomer or linked to a nucleoside.

Modified oligodeoxynucleotides complementary to the RNA of human immunodeficiency virus 1 (HIV-1) were synthesized by Agrawal, S., et. al., *Proc. Natl. Acad. Sci, U.S.A.*, 1988, 85, 7079–7083). Among the modifications disclosed in this publication are phosphoramidate oligonucleotides. Groups attached to these phosphoramidates include butylamine, piperazidine, and morpholine. The interactions of these compounds to their target, i.e. RNA, was through an antisense mechanism utilizing normal Watson/Crick hydrogen bonding. Similar phosphoramidate containing oligonucleotides are further disclosed by Dagle, et. al., *Nucleic Acids Research*, 1990, 18, 4751.

Phosphoramidate oligonucleotides are also disclosed in European Patent Application 86307926.5, filed Oct. 14, 1986. In this patent, a number of functional groups are used for substituting onto the phosphoramidate nitrogen. As with others of the above referenced disclosures, again in this patent the groups linking the phosphoramidates are nucleosides of oligonucleotides.

A family of oligonucleotides of different lengths containing a cholesterol group or phenanthridinium group tethered via a phosphoramidate bond to an internucleoside phosphorous atom were synthesized and tested for activity in an HIV-1 assay by Letsinger, R. L., et. al., *Proc. Natl. Acad. Sci. U.S.A.*, 1989, 86, 6553–6556). Two corresponding United States patents, U.S. Pat. Nos. 4,547,569 and 4,958,013, describes essentially the same structures.

In U.S. Pat. No. 5,218,103, issued Jun. 8, 1993, phosphorothioamidate oligonucleotides are disclosed. The phosphorothioamidate oligonucleotides disclosed in this patent are substituted with a variety of moieties on the phosphorothioamidate nitrogen.

In U.S. Pat. No. 5,362,899, issued Nov. 8, 1994, a stereospecific method of preparing alpha-aminophosphonic acids and derivatives thereof is disclosed.

In each of the foregoing disclosures, it is not known to use phosphoramidate linkage between any groups other than the nucleoside residues of oligonucleotides.

OBJECTS OF THE INVENTION

It is an object of this invention to provide novel phosphoramidate oligomeric compounds.

It is a further object of this invention to provide novel phosphorothioamidate oligomeric compounds.

It is yet a further object of this invention to provide novel phosphoramidate and phosphorothioamidate oligomeric compounds having fixed sequenced functional groups thereon.

It is yet a further object of this invention to provide novel phosphoramidate and phosphorothioamidate oligomeric compounds having random by sequenced functional groups thereon. Another aspect of the invention is to provide highly diverse chemical libraries.

BRIEF SUMMARY OF THE INVENTION

The present invention provides compounds of the structure I:

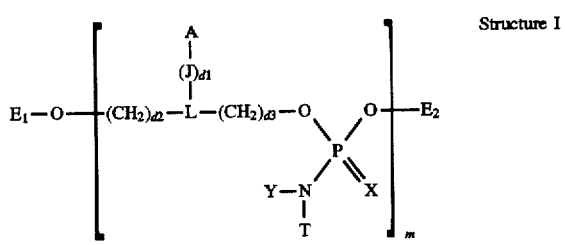

Structure I wherein
each X, independently, is O or S;
each Y, is $[Q_2]_j$—$Z_2$;
each T, independently, is $[Q_1]_k$—$Z_1$, or together Y and T are joined in a nitrogen heterocycle;
$Q_1$, $Q_2$, and each L, independently, is $C_2$–$C_{10}$ alkyl, $C_2$–$C_{10}$ alkenyl, $C_2$–$C_{10}$ alkynyl, $C_4$–$C_7$ carbocyclo-alkyl or -alkenyl, a heterocycle, an ether having 2 to 10 carbon atoms and 1 to 4 oxygen or sulfur atoms, a polyalkylene glycol, or $C_7$–$C_{14}$ aralkyl, provided that when L is a heterocycle, that at least one L is not a substituted pyrrolidine or a native nucleobase, and that when L is alkyl, that at least one L is not a substituted glycol; $E_1$ and $E_2$, independently, are H, a hydroxyl protecting group, an activated solid support, a conjugate group, a reporter group, a polyethylene glycol, alkyl, oligonucleotide, peptide nucleic acid, a phosphate, a phosphite, an activated phosphate, or an activated phosphite;
j and k independently are 0 or 1;
m is 2 to about 50;
$Z_1$ and $Z_2$, independently, are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, a halogen, CH=O, $OR_1$, $SR_2$, $NR_3R_4$, C(=NH)$NR_3R_4$, CH($NR_3R_4$), NHC(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;
A is $L_1$, $L_1$–$G_1$, $L_2$, $L_2$–$G_2$, $NR_3R_4$, H, a nitrogen-containing heterocycle, a purine, a pyrimidine, a phosphate group, a polyether group, or a polyethylene glycol group;
J is $L_1$, $G_3$, $L_1$–$G_3$ or $G_3$–$L_1$–$G_3$;
$L_1$ is alkyl having 1 to about 20 carbon atoms, alkenyl having 2 to about 20 carbon atoms, or alkynyl having 2 to about 20 carbon atoms;
$L_2$ is aryl having 6 to about 14 carbon atoms or aralkyl having 7 to about 15 carbon atoms;
$G_1$ is halogen, $OR_1$, $SR_2$, $NR_3R_4$, C(=NH)$NR_3R_4$, NHC(=NH)$NR_3R_4$, CH=O, C(=O)$OR_5$, CH($NR_3R_4$)(C(=O)$OR_5$), C(=O)$NR_3R_4$, a metal coordination group, or a phosphate group;
$G_2$ is halogen, OH, SH, $SCH_3$, or $NR_3R_4$;
$G_3$ is C (=O), C(=S), C(O)—O, C(O)—NH, C(S)—O, C(S)—NH or S(O)$_2$;
each d1, independently, is 0 or 1;
each d2, independently, is from 0 to 6;
each d3, independently, is from 1 to 6;
$R_1$ is H, alkyl having 1 to about 6 carbon atoms, or a hydroxyl protecting group;
$R_2$ is H, alkyl having 1 to about 6 carbon atoms, or a thiol protecting group;
$R_3$ and $R_4$ are, independently, H, alkyl having 1 to about 6 carbon atoms, or an amine protecting group; and
$R_5$ is H, alkyl having 1 to about 6 carbon atoms, or an acid protecting group.

The invention further includes chimeric oligomeric compounds having a first region comprising a phosphodiester or phosphorothioate oligonucleotide and a second region comprising a region having Structure I above and where one of $E_1$ and $E_2$ groups of the Structure I region of the chimeric compound is the phosphodiester or phosphorothioate oligonucleotide and the other of the $E_1$ and $E_2$ groups is H. In further chimeric oligomeric compounds, the phosphodiester or phosphorothioate oligonucleotide region of the chimeric compound is positioned between two regions, each of which is a region having the Structure I above.

DETAILED DESCRIPTION OF THE INVENTION

Compounds of the invention are shown by Structure I above. In Structure I, the bracketed portion is herein referred to as a monomeric unit. A monomeric unit is comprised of a backbone segment with a phosphoramidate or phosphorothio-amidate attached thereto. Compounds of the present invention are made up of at least 2 of these monomeric units. Included in a monomeric unit is a phosphoramidate or phosphorothioamidate moiety that, in turn, is capable of bearing functional groups thereon. The phosphoramidate or phosphorothioamidate moiety is covalently bonded to a backbone segment which may also be capable of including a variety of functional groups covalently bonded thereto. Functional groups are covalently bonded directly to the backbone segment and the phosphoramidate or phosphorothioamidate, or via an optional tether group.

The backbone segment and phosphoramidate moiety or phosphorothioamidate moiety serve as sites for connecting certain other groups that impart "functional" properties to the oligomeric compounds of the invention. By varying these functional groups—diversity is incorporated into the compounds of the invention.

In preferred embodiments of the invention functional groups are connected to phosphoramidate and phosphorothioamidate moieties preferably utilizing H-phosphonate or H-phosphorothioamidate intermediates. Functional groups are connected to these intermediates by an oxidation mechanism—that is oxidizing the H-phosphonate or H-phosphorothioamidate intermediates to the final phosphoramidate or phosphorothioamidate states.

For the purposes of this specification, in the context of the invention and in reference to the above Structure I, alkyl, alkenyl, and alkynyl groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl, which has further straight or branched chains attached to the carbon atoms of the straight chain. A cyclic compound, as used herein, refers to closed chain compounds—that is, a ring of carbon atoms, such as a cyclic aliphatic or aromatic compound. The straight, branched, or cyclic compounds may be internally interrupted (i.e., alkylalkoxy or heterocyclic compounds). In the context of this invention, internally interrupted means that the carbon chains may be interrupted with heteroatoms such as O, N, or S; however, if desired, the carbon chain may have no heteroatoms.

Such compounds as noted above may be substituted or unsubstituted. In the context of this invention, substituted or unsubstituted, means that the compounds may have any one of a variety of substituents, in replacement, for example, of one or more hydrogen atoms in the compound, or may have no substituents. Functional groups according to the invention include but are not limited to halogen (Cl, Br, F), hydroxyl (OH), thiol (SH), keto (C=O), carboxyl (COOH), ethers, thioethers, amidine (C(=NH)NR$_3$R$_4$, guanidine (NHC(=NH)NR$_3$R$_4$, glutamyl CH(NR$_3$R$_4$) (C(=O)OR$_5$), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH$_2$), azido (N$_3$), hydrazino (NHNH$_2$), hydroxylamino (ONH$_2$), sulfoxide (SO), sulfone (SO$_2$), sulfide (S—), disulfide (S—S), silyl, heterocyclic, alicyclic and carbocyclic. Preferred functional groups include halogens, alcohols and ethers (OR$_1$), thiols and thioethers (SR$_2$), amines (NR$_3$R$_4$), amidines [C(=NH)NR$_3$R$_4$], guanidines [NHC(=NH) NR$_3$R$_4$], aldehydes (CH=O), acids [C(=O)OH], esters [C(=O)OR$_5$], amides [C(=O)NR$_3$R$_4$] and glycine [CH(NH$_2$)(C(=O)OH)].

The above groups Y, T and A which represent functional groups, can be referenced as "letters." The use of such terminology reflects the fact that the different functional groups on the backbone segment and phosphoramidate moiety or phosphorothioamidate moiety are positioned in sequences (either predetermined or by random selection) much like letters of the alphabet—thus the term "letter." These letters can be "reactive" or "non-reactive." By reactive, it is meant that they will interact with a target molecule in some manner (that need not but can be predefined). By non-reactive, it is meant that they are not designed to primarily interact with a target molecule, and in fact while they may interact with the target molecule, the primary purpose of the non-reactive moieties are to impart other properties to the molecule such as, but not necessary limited to, effecting up-take, distribution, metabolism or identification.

Reactive functionalities used as letters, suitable for use in the practice of this invention include, but are not limited to, halogens; substituted or unsubstituted heterocyclic compounds, such as substituted or unsubstituted heterocycloalkyls; amino containing groups, such as heterocycloalkyl-amines, polyalkylamines, imidazoles, imadiazole amides, alkylimidazoles; substituted or unsubstituted aldehydes; substituted or unsubstituted ketones; substituted or unsubstituted ethers; substituted or unsubstituted esters; substituted or unsubstituted aryl compounds having from about 6 to about 20 carbon atoms, such as aralkylamino having from about 6 to about 20 carbon atoms, aminoaralkylamino having from about 6 to about 20 carbon atoms, alkyloxyaryl compounds, or allyloxyaryl compounds.

The functional groups are attached to the backbone segment and phosphoramidate moiety or phosphorothioamidate moiety with or without intervening tethers. Tethers, as used in the context of this invention, are bivalent or polyvalent groups that have a primary or secondary amine or other suitable group to react with an H phosphonate, H phosphonothioate or backbone segment of the invention together with a second functional group capable of binding a "letter". Such tethers can be used to position "letters" in space with respect to the linear backbone of the oligomeric compound synthesized or to link letters that themselves do not include an amine group—necessary to form a phosphoramidate linkage—as an inherent part of the letter. A particularly preferred group of compounds, when substituted with an appropriate amine functional group where necessary, useful as tethers include, but are not limited to $C_2$–$C_{10}$ alkyl, $C_2$–$C_{10}$ alkenyl, $C_2$–$C_{10}$ alkynyl, $C_4$–$C_7$ carboccylo-alkyl or alkenyl, heterocycles, an ether having 2 to 10 carbon atoms and 1 to 4 oxygen or sulfur atoms, polyalkylene glycols and $C_7$–$C_{14}$ aralkyl groups. Other representative tethers useful in the practice of the invention are disclosed in U.S. application Ser. No. 08/116,801, filed Sep. 3, 1993, entitled "Thiol-Derivatized Nucleosides and Oligonucleosides" and U.S. application Ser. No. 117,363, filed Sep. 3, 1993, entitled "Amine-Derivatized Nucleosides and Oligonucleosides", the disclosures of which are hereby incorporated by reference.

Amines include amines of all of the above alkyl, alkenyl and aryl groups including primary and secondary amines and "masked amines" such as phthalimide. Amines of this invention are also meant to include polyalkylamino compounds and aminoalkylamines such as aminopropylamines and further heterocycloalkylamines, such as imidazol-1, 2, or 4-yl-propylamine.

Other reactive functionalities suitable for practicing the invention include, without limitation, compounds having thiol (SH), aldehyde (C=O), or alcohol (OH) functionalities.

Heterocycles, including nitrogen heterocycles, suitable for use as functional groups include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. Imidazole groups are especially preferred.

Purines and pyrimidines suitable for use as functional groups include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the Concise Encyclopedia Of Polymer Science And Engineering, pages 858–859, Kroschwitz, J. I., ed. John Wiley & Sons, 1990, and those disclosed by Englisch, et al., Angewandte Chemie, International Edition 1991, 30, 613.

Aryl groups according to the invention include but are not limited to substituted and unsubstituted aromatic hydrocarbyl groups such as phenyl and naphthyl groups. Aralkyl groups include but are not limited to groups having both aryl and alkyl functionality, such as benzyl and xylyl groups.

Metal coordination groups according to the invention include but are not limited to hydroxamic acids, catecholamide, acetylacetone, 2,2'-bipyridine, 1,10-phenanthroline, diacetic acid, pyridine-2-carboxamide, isoalkyldiamine, thiocarbamate, oxalate, glycyl, histidyl and terpyridyl. Other metal coordination groups are known, as for example see Mellor, D. P., *Chemistry of Chelation and Chelating Agents in International Encyclopedia of Pharmacology and Therapeutics*, Section 70, The Chelation of Heavy Metals, Levine, W. G. Ed., Pergamon Press, Elmford, N.Y., 1979.

Non-reactive functionalities used as letters, such as groups that enhance pharmacodynamic properties, include groups that improve uptake, enhance resistance to degradation, and/or strengthen sequence-specific interaction with a target molecule. Non-reactive functionalities may also enhance pharmacokinetic properties, in the context of this invention, such groups improve uptake, distribution, metabolism or excretion. Non-reactive functionalities include, but are not limited to, alkyl chains, polyamines, ethylene glycols, polyamides, aminoalkyl chains, amphipathic moieties, points for reporter group attachment, and intercalators attached to any of the preferred sites for attachment, as described above.

Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene.

A number of functional groups can be introduced into compounds of the invention in a blocked form and subsequently de-blocked to form a final, desired compound. In general, blocking groups render chemical functionality inert to specific reaction conditions and can be appended to and removed from such functionality in a molecule without substantially damaging the remainder of the molecule. See, e.g., Green and Wuts, *Protective Groups in Organic Synthesis*, 2d edition, John Wiley & Sons, New York, 1991. For example, amino groups can be blocked as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl)xanthine-9-yl (MOX).

In the compounds of the invention, as noted above, in certain embodiments E1 and E2 are selected as conjugate groups. Conjugate groups of the invention include reporter enzymes, reporter molecules, steroids, carbohydrates, terpenes, peptides, proteins, aromatic lipophilic molecules, non aromatic lipophilic molecules, phospholipids, intercalators, cell receptor binding molecules, crosslinking agents, water soluble vitamins, lipid soluble vitamins, RNA cleaving complexes, metal chelators, porphyrins, alkylators, polymeric compounds such as polymeric amines, polymeric glycols and polyethers and others. Typical conjugate groups include cholesterols, phospholipids, biotin, phenanthroline, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA.

Groups that enhance the pharmacokinetic properties, in the context of this invention, include groups that improve oligomer uptake, distribution, metabolism or excretion. Representative conjugate groups are disclosed in international Patent Application PCT/US92/09196, filed Oct. 23, 1992, U.S. patent application Ser. No. 116,801, filed Sep. 3, 1993, now U.S. Pat. No. 5,578,718, and U.S. Pat. No. 5,218,105. Each of the foregoing is commonly assigned with this application. The entire disclosure of each is incorporated herein by reference.

In other aspects of the present invention the use of acid labile groups which are stable to the trichloroacetic acid treatment used for DMT removal, BOC-type protecting groups can preferably used. They are stable to extended TCA treatment, but are removed, such as by trifluoroacetic acid solutions 5% in $CH_2Cl_2$). Another protecting group class which is compatible to this methodology is the Allyl class. These groups are cleaved using transition metal catalysts. This type of protecting group is particularly valuable in cases where the selective deprotection of a particular functional group is desired while the oligomer is still attached to the solid support, allowing a new reactive site to be uncovered. Additional protecting group tactics are possible: e.g. photolabile protecting groups are also compatible with this methodology.

In structure I, $E_1$ and $E_2$ are the ends of the oligomer which is m monomeric units long. During synthesis, the ends are in fact working ends, e.g. can be used to link the structure to a solid support or the like and can be used to extend the oligomeric structures.

In a preferred solid phase synthesis, $E_1$ is selected to be an activated solid support and $E_2$ is selected to alternate, as the synthesis proceeds, between a protecting group or hydrogen. L, as noted above, is a backbone segment which directly or through methylene or other groups is bonded to a phosphoramidate or phosphorothioamidate moiety to which functional groups, A can also be bonded. As noted before, the functional group A may include an optional tether group designated J in structure I. Y is typically a hydrogen but can be a tethered or untethered functional group. T is hydrogen, a tethered or untethered functional group or together with Y form a nitrogen containing heterocycle about nitrogen. A, T and Y, are the above defined "letters."

X is either oxygen or sulfur. When X is O, the compounds of the invention are identified as phosphoramidates. When X is S, the compounds are identified as phosphorothioamidates. In certain embodiments, each X will be O. In other embodiments, each X will be S. In other embodiments, mixtures of O and S are both included in a compound of the invention.

Oligomeric compounds of the invention can be synthesized with the sequence of letters predetermined or random. Thus in certain preferred embodiments, the sequence of letters is a predetermined sequence. In further preferred embodiments, the sequence of letters is random. In even further preferred embodiments, the sequence is modulated between fixed and random. This is especially useful, as for example, in certain combinatorial strategies such as the above referenced SURF strategy.

A further advantage of this invention is the ability to synthesize oligomeric compounds that, in addition to or in place of variability in the sequences of the letters, have an asymmetric sequence of backbone segments. Stated otherwise, the backbone segments can also vary within an oligomeric structure. This is easily accomplished by using different dehydrase compounds that eventually become incorporated as backbone segments.

One preferred method of synthesizing the compounds of the invention is via a solid phase synthesis. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J., 1993.)

A preferred solid phase synthesis utilizes H phosphonates and H phosphonothioates as activated phosphites. The chemistry of the phosphorous atom in H phosphonates and H phosphonothioates is $P^{III}$. The intermediate compounds are subsequently oxidized to the $P^V$ state in the presence of a primary or secondary amine attached to a letter. The letter is attached to a primary or secondary amine either with or without a tether. Certain nitrogen containing heterocycles are used as the attaching moiety wherein the nitrogen is covalently bound to phosphorous. In addition to solid phase synthesis, solution phase synthesis can also be utilized to synthesize the compounds of the invention. Solution phase chemistry is accommodated by attaching a base labile protecting group e.g. FMOC, TBDMS, or TPDMS to $E_1$.

Hydrogen phosphonate chemistry has the advantage of allowing additional chemical modifications to be introduced into oligomers. Oligonucleotide phosphodiesters and phosphorothioates have been prepared using this approach,(see Froehler, B. C., Matteucci, M. D. *Tetrahedron Lett.* 1986, 27, 469–472), as well as oligonucleotide phosphoramidates (see Froehler, B. C. *Tetrahedron Lett.* 1986, 27, 5575–5579. Letsinger, R. L., Singman, C. N., Histand, G., Salunkhe, M. *J. Am. Chem. Soc.* 1988, 110, 4470–4471. The synthesis of oligomers containing both phosphodiesters and phosphoramidates was reported, as well as the use of phosphoramidite chemistry in conjunction with the synthesis of phosphoramidates (see Jung, P.M., Histand, G., Letsinger, R. L. *Nucleosides & Nucleotides*, 1994, 13, 1597–1605). In this latter work, alternating phosphodiester and phosphoramidate oligomers were prepared by coupling phosphoramidites and H-Phosphonates to a growing oligomer, followed by the appropriate oxidation step. In general, however, all the examples described heretofore have incorporated the same amine substitution at all phosphoramidate linkages in the oligomer.

However, these studies have shown the feasibility of using the phosphoramidate bond as an additional site for the incorporation of diverse functional groups. A wide variety of amines can be used in the oxidative step, and the monomers of the present invention support the necessary chemistry. Thus, for the preparation of combinatorial libraries incorporating phosphoramidate linkages, the monomers of the present invention are converted to the corresponding H-Phosphonate monoesters. In one aspect of the present invention this was accomplished using $PCl_3$ and imidazole as the phosphitylating reagent (see Garegg, P. J., Regberg, T., Stawinski, J., Strömberg, R. *Chem. Scr.* 1986, 26, 59–62). These H-phosphonates monomers are oligomerized on solid support by activation with pivaloyl chloride, adamantoyl chloride or other appropriate activating agent. The intermediate H-Phosphonate diesters can be oxidized to the phosphate diesters in high yields e.g., using iodine in aqueous pyridine. This allows for the comparison of the coupling efficiency of the H-phosphonate and phosphoramidite methods. Essentially the same coupling efficiency is achieved with both methodologies. The H-phosphonate diesters are converted to phosphoramidates by the use of a 10% solution of the appropriate amine in pyridine/$CCl_4$ (1:1). Under these conditions, a H-phosphonate diester is oxidized to a phosphoryl chloride via an Arbuzov reaction, followed by displacement of the chloride by a primary or secondary amine. The second step has proven to be quite general, with a wide variety of amines giving satisfactory yields. Moreover, the yield of phosphoramidate is comparable to the yield of phosphodiester.

Several types of libraries are available through this methodology. The simplest kind is a library made from a set of monomers of the present invention (a set of 4 to 16 or more backbone segments is typically used) of 2 to 10 or more monomeric units in length, which are substituted at phosphorus with a single amine may be substituted with a single letter on the backbone positions (($J$)$_{d_1}$ and A). Letters may include optional tether groups. These libraries can be prepared by split bead synthesis, following the H-phosphonate synthesis protocol rather than phosphoramidite chemistry. The intermediate H-phosphonate diesters are left intact until the final step. At that point the oligomer library pools are oxidized with CCl$_4$/Pyridine containing 10% of the appropriate primary or secondary amine. This has the result of converting all the interresidue linkages to phosphoramidates.

When the final oligonucleotide also has "letters" on the backbone, e.g. the ($J$)$_{d_1}$ and A positions, the protecting groups on the positions to be randomized can be removed with a conventional reagent. The individual pools are treated with the "letter" in a convenient solvent. To facilitate high yields, a coupling agent will often be used. Some commercially available coupling reagents are benzotriazol-1-yloxy-tris(dimethyl-amino)phosphonium hexafluorophosphate, [O-(7-azabenzotriazol-1-yl)-1,1,3,3-tetramethyluronium hexafluorophosphate, HoBt, and PyBOP. The library therefore is composed of all possible sequences of the monomers, separated into subsets unique at a fixed position, linked together by a constant phosphoramidate linkage. It should be evident that the final properties of the library will be determined by the choice of amine used in the oxidation step and also by the letter bound to the backbone if present. Thus, water solubility, pharmacokinetics and pharmacodynamics of the library components can be modulated by the choice of amine and letter.

It is also possible to prepare oligomer libraries with mixed linkages by having an intermediate oxidation step (see Gryaznov, S. M., Sokolova, N. I. *Tetrahedron Lett.* 1990, 31, 3205–3208; Gryaznov, S. M., Potapov, V. K. *Tetrahedron Lett.* 1991, 32, 3715–3718; Farooqui, F., Satin, P.S., Sun, D., Letsinger, R. L. *Bioconjugate Chem.*, 1991, 2, 422–426; Iso, Y., Yoneda, F., Ikeda, H., Tanaka, 503–506). Thus, a portion of the oligomer library is synthesized by H-phosphonate chemistry, which can be oxidized with (R$_2$NH, CCl$_4$/Py or S8, CS$_2$/TEA or H$_2$O, CCl$_4$/Py), and a second portion of the library synthesized and oxidized with a second set of reagents. This creates a chimeric library, where a segment of the random oligomers in each subset has a different linkage than the rest of the molecule. By extension of this methodology, it is possible to incorporate a different linkage at each position of the oligomer library by having a different oxidation step after each monomer coupling. It is also possible to incorporate a different letter in each backbone segment by adding a deprotection step and a coupling step following each oxidation step. The linkage can be combinatorialized by performing a separate oxidation on a portion of the phosphonate diester-linked solid support, followed by pooling of the subsets in the same way that the monomer positions are randomized. Thus, each monomer and the linkage between them can be randomized by a split synthesis strategy.

"Letters" are attached to their respective amino groups, which are in turn, attached to phosphite groups to form the phosphoramidate and phosphorothioamidates of the invention. One preferred method of effecting this attachment is via oxidation. Oxidation of the H phosphonate or H phosphonothioate intermediates of the invention in the presence of functional groups attached with or without a tether to a primary or secondary amine will form the phosphoramidates or phosphorothioamidates. These functional groups thus provide diverse properties ("diversity") to the resulting oligomeric compounds. The functional groups include hydrogen-bond donors and acceptors, ionic moieties, polar moieties, hydrophobic moieties, aromatic centers, and electron-donors and acceptors. Together, the properties of the individual repeating monomeric units contribute to the properties of the oligomer in which they are found. Thus, a library of such oligomers would have a myriad of properties, i.e., "diversity." Collectively, the properties of the monomeric units that form an oligomer contribute to the properties of such an oligomer and impart certain characteristics thereto for interaction with cellular, enzymatic or nucleic acid target sites.

To synthesize a combinatorial library having a large degree of chemical diversity is an important aspect of the present invention. Chemical diversity is introduced at one level by varying the nature of the phosphorus likage. Phosphorus linkages amenable to the present invention include phosphoramidate (OPN) and phosphorothioamidate (SPN). Combinatorial libraries can be prepared with a single type of phosphorus linkage, or with a mixture of SPN and OPN linkages at each position of the oligomer. For example, a single OPN linkage can be selectively introduced at any position in a SPN oligomer. In fact, all possible combinations of SPN and OPN linkages can be introduced selectively into oligomers of the invention. The presence or absence of a type of linkage at a particular position in an oligomer can have a profound effect on the properties of the molecule.

Chemical diversity can be generated at several levels in SURF libraries. We have described below the preparation of monomers. These monomers have been prepared to explore two aspects of chemical diversity: first a wide number of functional groups are available, covering a range of chemical properties. Second, these functional groups can be attached to different tethers designed to display, or present them in space in different ways, allowing variable flexibility. The following section describes a third level of diversity, the inter-residue linkage itself. By using the proper conditions, it is possible to introduce phosphoramidate or phosphorothioamidate linkages at any position in an oligomer, independently of the sequence of the oligomer.

In the case of a phosphoramidate linkage, removal of the DMT group or other suitable protecting group from the hydroxyl of the derivatized solid support or the last monomeric unit that has been attached followed by treatment of the free hydroxyl under standard conditions with a phosphonic acid derivatized backbone segment will give the H-phosphonate diester. Oxidation of the H-phosphonate such as by using a 10% solution of the appropriate amine in pyridine/CCl$_4$ (1:1), will give the phosphoramidate.

In the case of a phosphorothioamidate linkage, removal of the DMT group or other suitable protecting group from the hydroxyl of the derivatized solid support or the last monomeric unit that has been attached followed by treatment of the free hydroxyl with a phosphorodiamidite derivatized backbone segment such as under the conditions of Example III of U.S. Pat. No. 5,218,103, will give a disubstituted phosphoramidite. Further treatment of the resulting disubstituted phosphoramidite with H$_2$S and tetrazole such as per Example III of U.S. Pat. No. 5,218,103, will give the H-phosphonothioate. Oxidation of the H-phosphonothioate in the presence of an amine "letter" such as per Example VI of U.S. Pat. No. 5,218,103, will give the phosphorothioamidate.

The oligomeric compounds of the invention can be prepared having either preselected sequences or sequences determined via combinatorial strategies. One useful combinatorial strategy is the above-noted SURF strategy, which is disclosed and claimed in U.S. patent application Ser. No. 749,000, filed Aug. 23, 1991, now abandoned, and PCT Application US92/07121, filed Aug. 21, 1992, both of which are commonly assigned with this application. The entire disclosure of these applications are herein incorporated by reference.

Illustrative of the SURF strategy is a 2'-O-methyl oligonucleotide library (see, Ecker et. al., ibid.) shown in Table I, below. Table I describes the selection of a 2'-O-methyl oligonucleotide for binding to an RNA hairpin. The $K_D$'s, i.e., the binding constants, were determined by gel shift. "X" is used to indicate the position being varied and underlining is used to indicate positions that become fixed during successive iterations of the SURF strategy.

TABLE I

| Subsets | $K_D$ (mM) X = A X = C X = G X = T |
|---|---|
| Round 1 | |
| NNNNXNNNN | 22<u>10</u> > 100 > 100 |
| Round 2 | |
| NNNN<u>C</u>NXNN | >10<u>4</u> > 10 > 10 |
| Round 3 | |
| NNXN<u>C</u>N<u>C</u>NN | >10<u>0.5</u> > 10 > 10 |
| Round 4 | |
| NN<u>C</u>X<u>C</u>N<u>C</u>NN | >10<u>0.15</u> > 10 > 10 |
| Round 5 | |
| NN<u>CCC</u>X<u>C</u>NN | 0.<u>08</u> > 10.4 > 1 |
| Round 6 | |
| NN<u>CCC</u>A<u>C</u>XN | 0.<u>05</u> > 0.50.08 > 0.5 |
| Round 7 | |
| NX<u>CCC</u>A<u>C</u>AN | >0.1 >0.1<u>0.03</u> > 0.1 |
| Round 8 | |
| N<u>GCCC</u>A<u>C</u>AX | 0.05<u>0.02</u>0.050.04 |
| Round 9 | |
| X<u>GCCC</u>A<u>C</u>AC | 0.030.050.02<u>0.01</u> |

This SURF strategy has not been previously used for libraries except those that employ naturally-occurring nucleotides as phosphodiesters or phosphorothioates as monomeric units. Other combinatorial strategies have only been previously used for libraries that employ amino acids as monomeric units.

One aspect of the present invention is the inclusion of oligomeric structures of the invention having Structure I in the above-described SURF or other combinatorial strategies. The functional groups appended to these oligomeric structures can be incorporated into libraries while retaining the advantages of automated phosphoramidate or phosphorothioamidate oligomer synthesis. In one aspect of the present invention the interactions effected by these functional groups are of the following types: hydrogen-bond donor and acceptor, ionic, polar, hydrophobic, aromatic, and electron donors and acceptors. Preferred functional groups include aminoethyl, carboxyethyl, adenylmethyl, thyminylmethyl, imidazolylmethyl, benzyl, myristyl, isopropyl, and tetraethylene glycol groups.

One advantage of the present invention is that the simple design of monomeric units enables combining rational drug design with screening mechanisms for thousands of compounds. This is achieved by using the compounds of the invention in a combinatorial techniques such as the SURF strategies. A preferred target molecule for utilizing such combinatorial techniques is the phospholipase $A_2$ family.

Phospholipases $A_2$ ($PLA_2$) are a family of enzymes that hydrolyze the sn-2 ester linkage of membrane phospholipids resulting in release of a free fatty acid and a lysophospholipid (see, Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (see, e.g., Dennis, ibid.; Glaser, et al., TiPs Reviews 1992, 14, 92; and Pruzanski, et al., Inflammation 1992, 16, 451).

All mammalian tissues evaluated thus far have exhibited $PLA_2$ activity. At least three different types of $PLA_2$ are found in humans: pancreatic (type I), synovial fluid (type II) and cytosolic. Studies suggest that additional iso-enzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath, et al., Inflammation 1988, 12, 549) or into the articular space of rabbits (Bomalaski, et al., J. Immunol. 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g., pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott, et al., Science 1990, 250, 1541). Recently, the crystal structure of $PLA_2$ from human synovial fluid has been solved (Wery, et. al., Nature 1991, 352, 79). The structures clarify the role of calcium and amino acid residues in catalysis. The calcium acts as a Lewis acid to activate the scissile ester carbonyl of 1,2-diacylglycerophospholipids and bind the lipid, and a His-Asp side chain dyad acts as general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged aminoterminal helix is situated above the opening of the hydrophobic cleft. Several lines of evidence suggest that the N-terminal portion is the interfacial binding site. (see, e.g., Achari, et al., *Cold Spring Harbor Symp. Quant. Biol.* 1987, 52, 441; Cho, et al., *J. Biol. Chem.* 1988, 263, 11237; Yang, et al., *Biochem. J.* 1989, 262, 855; and Noel, et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. The evidence favoring this hypothesis comes from studies revealing that rapid changes in $PLA_2$ activity occur concurrently with changes in the fluorescence of a membrane probe (Burack, et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger, et al., *FEBS Lett.* 1989, 252, 73). These studies clearly show that $PLA_2$ binds exclusively at the boundary region between liquid and solid phase lipid.

While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e., phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (see, e.g., Yuan, et al., *J. Am. Chem. Soc.* 1987, 109, 8071; Lombardo, et al., *J. Biol. Chem.* 1985, 260, 7234; Washburn, et al., *J. Biol. Chem.* 1991, 266, 5042; Campbell, et al., *J. Chem. Soc., Chem. Commun.* 1988, 1560; and Davidson, et al., *Biochem. Biophys. Res. Commun.* 1986, 137, 587), reports describing in vivo activity are limited (see, e.g., Miyake, et al., *J. Pharmacol. Exp. Ther.* 1992, 263, 1302).

In one preferred embodiment, functional groups appended to the monomeric units of the invention are selected for their potential to interact with, and preferably inhibit, the enzyme $PLA_2$. Thus, the compounds of the invention can be used for topical and/or systematic treatment of inflammatory diseases including atopic dermatitis and inflammatory bowel disease.

In selecting the functional groups, advantage can be taken of $PLA_2$'s preference for anionic vesicles over zwitterionic vesicles. Further advantage can also be taken of the compounds of the invention having phosphate groups since the natural substrate of $PLA_2$ contains a phosphate group.

Certain compounds of the invention include aromatic functional groups to facilitate binding to the cleft of the $PLA_2$ enzyme. (see, Oinuma, et al., *J. Med. Chem.* 1991, 34, 2260; Marki, et al., *Agents Actions* 1993, 38, 202; and Tanaka, et al., *J. Antibiotics* 1992, 45, 1071). Benzyl and 4-hexylbenzyl groups are preferred aromatic groups. The compounds of the invention can further include hydrophobic functional groups such as tetraethylene glycol groups. Since the $PLA_2$ enzyme has a hydrophobic channel, hydrophobicity is believed to be an important property of inhibitors of the enzyme.

The $PLA_2$ assay can be effected using a combinatorial screening strategy such as the SURF strategy. For this assay, the oligomer libraries are screened for inhibition of human type II $PLA_2$ enzymatic activity. Typically, these libraries contain about 8000 different compounds. Successive iterations of the SURF technique is effected to select unique oligomers from the library. The libraries additionally can be screened in other in vitro assays to determine further mechanisms of inhibition.

To maximize the identification of a tight binding oligomeric inhibitor of $PLA_2$ via a combinatorial approach, an array of functional groups typically are included in a randomized library. The oligomers are assembled in a manner similar to oligonucleotide synthesis, by such as interative coupling of monomeric, H phosphonate and phosphorodiamidite derivatized backbone segments, preferably followed by the appropriate treatment previously described above in the case of the phosphorodiamidite derivatized backbone segment and followed by an oxidation step to effect the conversion to the phosphoramidate or phosphorothioamidate which may also have functional groups attached thereto.

In one embodiment of the invention, further functional groups are attached to the backbone segment. In certain other embodiments of the invention the region of space normally occupied only by nucleobases will be occupied by nucleobases in addition to other functional groups selected to provide different ligand-ligand interactions, than that provided by the nucleobases. This methodology provides for a convergent preparation of a large number of monomers bearing a wide variety of functional groups. Where necessary, functional groups can be protected with base labile protecting groups to allow one-step deprotection of the oligomer upon completion of the synthesis.

In certain embodiments of the invention, monomeric units are incorporated into libraries of oligomeric compounds. Increasingly less complex subsets of oligomers can be identified in combinatorial screening techniques such as the above-described SURF technique by successive rounds of screens. In one preferred embodiment of the invention the backbone segments are held fixed and the functional groups are randomized. In another preferred embodiment of the invention the functional groups are held fixed and the backbone segments are randomized. In another preferred embodiment of the invention, the functional groups and the backbone segments are randomized simultaneously. In a more preferred embodiment of the invention a combinatorial library is prepared wherein the backbone segments are held fixed and the functional groups are randomized.

Upon identification of an active oligomer in a first phase of screening the letters of the most active oligomer are preferably further modified. For example, if a first phase of screening results in an active compound that contains a benzyl group as a "letter", then in a subsequent second phase of screening the activity of this compound will be compared to that of compounds containing modifications to this aromatic ring, e.g. the effect of substitutions. In a third phase of screening, the effect of randomizing backbone segments can be studied. In this way, structural activity can be identified in a stepwise manner to define increasingly more potent inhibitors of the enzymatic activity.

To detect an active sequence generated via a combinatorial technique, the concentration of the active molecule selected should be sufficiently great such that the molecule can be detected within the sensitivity of the chosen assay. As will be recognized, the number of unique oligomer sequences within a subset produced via a combinatorial technique depends on the length of the oligomer and the number of different monomeric units employed. The number of sequences can be determined by raising the number of monomeric units to a power equal to the number of random positions. This is illustrated in Table II. Table II also indicates the concentration of each sequence when the subset concentration is 100 µM, a typical high-test concentration. As a first approximation, the number of monomeric units and their length can be based upon an estimate of the expected $IC_{50}$ (i.e., a concentration at which 50% of enzyme activity is inhibited) that is desirable in a final oligomeric compound. For an expected $IC_{50}$ of 100 nM, the complexities shown in Table II are acceptable, that is, the libraries shown in Table II have complexities that would allow detection of a unique sequence with an $IC_{50}$ of about 100 nM or less.

TABLE II

Complexity of Libraries

| Length | Sequences nM Each Sequence Per Subset At 100 µM Subset |
|---|---|
| 5 Monomers | |
| 4-mer | 125800 |
| 5-mer | 625160 |
| 6 Monomers | |
| 4-mer | 216463 |
| 5-mer | 1,29677 |
| 7 Monomers | |
| 4-mer | 343291 |
| 8 Monomers | |
| 4-mer | 512195 |
| 10 Monomers | |
| 4-mer | 1,000100 |

If five letters are selected for a library consisting of uniform backbone segment length, then the library will have a length of five monomeric units and one backbone segment. The library will be substituted with letters XNNNN at phosphoramidate positions of the monomeric units where N is an equimolar mixture of letters and X is a different letter in each of the five subsets, and will have either no letters attached to the backbone segment or will be uniformly substituted with a single letter at each backbone segment. For ease of synthesis, the fixed position can be conveniently selected as the "right" hand end of the molecule. After assay for inhibition of activity, such as $PLA_2$ activity as described below, position X is fixed with the letter giving the greatest inhibition and the next subset is synthesized and screened. The fixed position then shifts towards the "left" end of the oligomer as unrandomization proceeds. Five rounds of synthesis and screening are conventional to determine a unique inhibitor. As described previously, the unique inhibitor can be further studied as to the effect of randomization of the backbone segment and the effect of randomizing a letter bound to the backbone segment.

The monomeric units of the invention can be linked to form oligomeric compounds using standard H phosphonate chemistry and in a like manner, H phosphonothioate chemistry, as has been used for synthesis of oligonucleotides. Since the coupling rates of letters will vary, in one embodiment of the invention, the reactivity of the individual letters bound to phosphoramidate or phosphorothioamidate positions is adjusted such that equal molar incorporation of each letter at each randomized position is effected. A technique for optimizing such adjustment is disclosed in the United States patent application entitled "Random Oligonucleotide Libraries And Methods Of Making The Same," Ser. No. 179,972, filed Jan. 11, 1994, now U.S. Pat. No. 5,587,471—also identified as attorney docket number ISIS-1009. The foregoing patent application is commonly assigned, and is incorporated herein by reference.

In a SURF screening strategy, the amount of oligomer is selected such that the concentration of each subset in the initial round of screening is relatively high (e.g. about 100 µM). It is presently preferred to synthesize oligomers using a DNA synthesizer. On such synthesizers the oligomers are most conveniently synthesized on a 1 to 4 µmol scale. Given the concentration of a subset of libraries at about 100 µm, the assays preferably are performed in a small volume of less than about 200 µL.

In the above noted Structure I, monomeric units (in brackets) can be linked with one another to form homopolymeric structures or they can be linked with nucleosides and/or other moieties to form heteropolymeric structures. For example, chimeric structures can be formed that include one or more regions or "stretches" of the monomeric units of the invention joined to one or more regions or "stretches" of naturally occurring or synthetic oligonucleotides or to other synthetic or natural oligomeric compounds such as peptides, peptoids, peptide nucleic acids, oligo and/or polysaccharides. Further, oligomeric compounds having structure I can be incorporated into chimeric structures along with the compounds disclosed in the patent application entitled "Monomeric Diols And Phosphate Linked Oligomers Formed Therefrom," Ser. No. 179,970, filed Jan. 11, 1994, also identified as attorney docket ISIS-0868 and the patent application entitled "Oligonucleotide Mimics Having Nitrogen-Containing Linkages," Ser. No. 180,124, filed Jan. 11, 1994, also identified as attorney docket ISIS-1014. The foregoing patent applications are filed concurrently with this application, are commonly assigned, and are incorporated herein by reference.

In one embodiment of the invention, oligomeric compounds as shown in Structure I, are synthesized having a fixed, predetermined sequence of "letters." In a further embodiment of the invention, oligomeric compounds are synthesized as shown in Structure I having random sequences. Further libraries of such randomly sequenced compounds can be prepared. This synthetic strategy emphasizes attachment of widely different functional groups to variable backbone segments or variable phosphoramidate or phosphorothioamidate positions to form the members of the library.

In one embodiment of the invention functional groups are appended to a phosphoramidate or a phosphorothioamidate diester oligomer. A backbone segment having two hydroxyl groups is protected using standard conditions (*Oligonucleotide Synthesis, A Practical Approach*, Gait, M. J., Ed., IL: New York., 1984, Chapter 1) with a dimethoxytrityl group or other suitable blocking group at one of the hydroxyls. This protected backbone segment is further reacted with succinic anhydride to form the protected backbone segment succinyl monoester. This monoester is activated with a leaving group e.g. pentafluorophenol or para nitrophenol, and derivatized onto a solid support e.g. LCAA CPG following standard methods.(M. J. Gait, ibid., Masad J. Damha, *nucleic acids research*, 1990, 18, 3813–3821). A capping step is performed using acetic anhydride to or other suitable capping agent to cap any remaining reactive sites. The DMT protecting group is removed with a dilute acid solution e.g. dichloroacetic acid or trichloroacetic acid thereby forming the deblocked backbone segment attached to solid support.

An H phosphonate mono ester-protected backbone segment is prepared by reacting a protected backbone segment with $PCl_3$ in the presence of imidazole or other suitable base following standard methods (*Nucleic Acids in Chemistry and Biology;* Blackburn, G. M., Gait M. J., Eds. Chemical Synthesis; IL: New York, 1990, Chapter 3, p. 98) to form a protected H phosphonate. The protected H phosphonate is isolated as a salt e.g. triethylammonium or DBU salt (Froehler, B., et. al., *Nucleic Acids Research*, 1988, 16, 4831–4838). The resulting protected H phosphonate monomeric unit, as a salt, is condensed onto the deblocked backbone segment attached to solid support to form the H phosphonate diester which is bound to solid support at one backbone segment and protected at the other backbone segment.

In one embodiment of the invention the H phosphonothioate diester is prepared by reacting a deblocked backbone segment attached to solid support prepared as above with bis(diisopropylamino)chlorophosphine in the presence of triethylamine or other suitable base following the method contained in U.S. Pat. No. 5,218,103 dated Jun. 8, 1993. The resulting intermediate is reacted with a protected backbone segment followed by treatment with hydrogen sulfide to form the H phosphonothioate diester which is bound to one backbone segment attached to a solid support and to another protected backbone segment.

"Letters" are covalently bound to an amino group with an optional tether group forming a primary amine in the case of a single letter or a secondary amine when 2 letters are covalently bound using known methods and techniques. The primary or secondary amine is attached to the H phosphonate diester or the H phosphonothioate diester via oxidation thereby forming a phosphoramidate or a phosphorothioamidate. By repeating the above steps a phosphoramidate or a phosphorothioamidate backbone oligomeric structure can be prepared with a predetermined sequence of letters. Furthermore, using backbone segments of different lengths and chemical complexity will add a second dimension to the diversity of the final compound.

The resulting oligomeric compound is cleaved from the solid support using standard conditions e.g. ammonium hydroxide. Detritylation with dilute acid will yield the final oligomeric compound.

Modification of the above steps enable the synthesis of oligomeric structures of the invention with a fixed/random sequence of letters covalently bound to the phosphoramidate or phosphorothioamidate group. Typically, an oligomeric structure is synthesized with one or more positions fixed and the other positions randomized. As testing proceeds, more positions are fixed and less are randomized until a unique compound is identified. Permutations of the above steps makes this possible.

To fix the first position or any number of positions starting from the solid support side of the compound the above steps are followed and the desired amine letter or letters are sequentially oxidized into the desired position as synthesis precedes. To randomize a single position with two or more amine letters, the selected letters are mixed together and the compound is oxidized with this mixture. To randomize two or more positions the oxidation step is omitted during that portion of the synthesis and these positions are oxidized in one step using a mixture of amine letters in the same manner as for one position e.g. more than one position can be oxidized simultaneously.

The concentration of individual amine "letters" in a mixture used for the oxidation step is adjusted for reactivity to ensure equal molar concentration in the final oligomer. To calculate the percentage of individual amine letters in an oligomeric structure it is necessary synthesize a test oligomeric compound using predetermined amine letters in equal molar amounts. The letters are cleaved from this oligomer with 10% formic acid at 50°–70° C. and analyzed by HPLC. The concentration of individual letters can be estimated from their known molar absorptivity. Alternatively, reaction of the oligomeric structure with phthalaldehyde and 2-thiolacetic acid will yield indole derivatives with high molar absorptivities (Bruckner, R., et al., *J. Chromatography*, 1989, 476, 73). This procedure has its greatest utility in those cases where the amine letter is not a UV-chromophore.

An alternative method of randomization is to effect the randomization of one position at a time during the synthesis of the oligomeric compound. The solid support is divided into equal portions to coincide with the number of amine letters that are being used for randomization. Each portion of the solid support is treated with a different letter separately. The solid support is recombined and another monomeric unit is added and the method is repeated until all the selected positions are randomized. The solid support is recombined for further synthesis. This method is referred to as bead splitting or resin splitting.

In certain combinatorial strategies, e.g. SURF, ibid, one letter is held fixed and the remaining positions are randomized. If the desired oligomer is a six mer—an oligomeric compound six units long—six oligomers are synthesized. The oligomers are synthesized on a DNA synthesizer in six separate runs. Each oligomer has one of six letters held fixed in the first position of the oligomer and the remaining positions are treated all at once with a mixture of the other five letters. As mentioned above the concentration of individual letters in a mixture is preadjusted with respect to reactivity to ensure equal molar ratios in each position on the oligomer. Alternatively, using bead splitting, the solid support can be separated into amounts equal to the number of letters in the mixture of letters and treated with each letter separately. This is done for each of the six libraries being prepared. When all the positions are randomized, the six resulting libraries of oligomers are tested in the assay of interest, as for example the above described $PLA_2$ assay, and the most active is determined. The oligomer that shows the most activity in this first round is chosen for a second round. In the second round the first position of all oligos is fixed with the letter that showed the most activity in round one. The second position is now fixed with the six letters as with the first run and the technique is repeated. Eventually a compound is identified from the last round where there are only six different oligomers in six assays.

In addition to randomizing letters, this invention also allows for variability in the backbone segments. The backbone segments, as seen in Structure I above, are used to connect the phosphoramidate or phosphorothioamidate moieties of the invention. The backbone segments thus "flank" the phosphoramidate or phosphorothioamidate moieties of the invention. In preferred embodiments of the invention, the precursor to the backbone segment is a polyol compound—the simplest being ethylene glycol. Using different backbone segment precursors, e.g. propylene glycol, butylene glycol or higher homologues, during oligomer synthesis will change the distance between phosphoramidate or phosphorothioamidate moieties lending a further level of diversity to the compounds of the invention. The rigidity of the backbone can also be modified by the use of cyclic structures and heterocycles.

The backbone segment can also contain functional groups that enhance the pharmacologic and other activities. More sophisticated units are envisioned to be within the scope of this specification. This variability adds a new dimension to the term randomization when compared to the current state of the art. When an active compound is identified and the functional groups are modified to maximize the activity, then backbone segment modification can be examined to further enhance the desired properties. This can be accomplished by modifying the synthesis of the phosphoramidates or phosphorothioamidate compounds simply by using different backbone segment precursors.

In a further embodiment of the present invention functional groups are attached to both the phosphoramidate or phosphorothioamidate group and the backbone segment of at least one of the monomeric units comprising an oligomer. A backbone segment having a protected reactive site such as a covalently bound nitrogen with a fluorenylmethylcarbonyl (fmoc) group is covalently bound to a solid support as described above. The reactive site is deprotected with a convenient reagent, such as piperidine in DMF for the Fmoc group, and a "letter" is coupled to the reactive site using a coupling agent. The protecting group on the solid support bound backbone segment is removed and an H phosphonate or a phosphorodiamidite covalently bound to a backbone segment having a protected reactive site is covalently bound thereto as described above.

Treatment of the phosphorodiamidite as described above will give the H phosphonothioate. The H phosphonate or the H phosphonothioate is oxidized in the presence of an amine "letter" to give the phosphoramidate of the phosphorothioamidate. The reactive site is deprotected with an appropriate reagent, such as piperidine in DMF for the Fmoc group, and a letter is coupled to the reactive site using a coupling agent. Repeating the procedures of adding an H phosphonate or a phosphorodiamidite covalently bound to a backbone segment having a protected reactive site through coupling a letter to the deprotected reactive site will effect the synthesis of an oligomeric compound of desired length and sequence of backbone segments, amine functional groups, backbone functional groups, and type of linkage e.g. phosphoramidate or phosphorothioamidate. The resulting oligomeric compound is cleaved from the solid support using standard conditions e.g. ammonium hydroxide. Detritylation with dilute acid will yield the final oligomeric compound.

The foregoing procedures above will enable a person skilled in the art to prepare oligomeric structures of the present invention having uniform or randomized backbone segments, backbone letters, amine letters, and linkage type. In one embodiment of the present invention, substantially all the backbone segments, backbone letters, amine letters, and linkage types are of a randomized from pools of synthons for the pertinent part of the monomeric units. In still another embodiment of the present invention oligomeric compounds comprised of monomeric units of Structure 1 are prepared having a predetermined sequence of backbone segments, backbone letters, amine letters, and linkage types. In another embodiment of the present invention at least one of the backbone segments, backbone letters, amine letters, and linkage types are held fixed while the remaining of the backbone segments, backbone letters, amine letters, and linkage types are randomized.

Oligomeric units bearing functional groups are prepared as per procedures described in the below examples. Reactive functional groups are appropriately blocked where necessary with a protecting group. Protecting groups are then removed upon completion of the synthesis of the oligomeric compound. Normally base labile protecting groups are used that are cleaved when the oligomer is removed from the resin.

EXAMPLE 1

2-O-(Dimethoxytrityl)ethanol

A solution of ethylene glycol (2.45 ml, 44 mmol) in dry pyridine (25 ml) was cooled to 0° C. in an ice bath. Excess triethylamine (7 ml) and 4-dimethylaminopyridine catalyst (120 mg, 1 mmol) was added followed by the slow addition of dimethoxytrityl chloride (7.42 g, 21.9 mmol) over 30 minutes. The mixture was stirred at 0° C. for 1 hr and then room temperature for 1 hr. The resulting solution was quenched with methanol and evaporated to dryness under reduced pressure. The residue was dissolved in saturated $NaHCO_3$ and extracted with EtOAc. The EtOAc extracts were washed with cold saturated sodium bicarbonate and brine. The organic phase is separated, dried over sodium sulfate, filtered and evaporated under reduced pressure. The resulting residue is purified by flash column chromatography on silica gel using ethyl acetate-hexanes (gradient 10 to 20%). The title compound was isolated to yield 5.53 g (70%). $^1$H NMR: ($CDCl_3$) δ7.50–7.20, 6.90–6.80 (m, 13 H, ArH), 3.80 (s, 6 H, $OCH_3$), 3.75 (t, 2H, $CH_2OH$), 3.25 (t, 2H, $DMTOCH_2$).

EXAMPLE 2

2-O-(Dimethoxytrityl)ethoxyphosphonic Acid

A solution of imidazole (4.29 g, 63 mmol)in dry acetonitrile at 0° C. (100 ml) was treated dropwise with $PCl_3$ (1.77 ml, 20.3 mmol) over a period of 30 minutes. The resulting solution is further treated with triethylamine (9.06 ml, 65 mmol). To the thick slurry was added 2-O-(dimethoxytrityl)ethanol (2.10 g, 5.81 mmol) in anhydrous acetonitrile (150 ml) slowly over a period of 30 minutes. The mixture is allowed to warm to room temperature and stirred for 15 minutes. The mixture is quenched with 1M TEAB and the mixture is evaporated in vacuo to a minimum volume and extracted with dichloromethane (2×150 ml). The dichloromethane extracts are washed with TEAB and evaporated in vacuo. The residue was purified by flash column chromatography using a gradient of 0% to 5% methanol in dichloromethane/1% triethylamine to yield 1.3 g purified material (43%). $^1$H NMR: ($CDCl_3$) δ 7.50–7.20, 6.90–6.80 (m, 13 H, ARE), 6.96 (d, 1H, $J_{PH}$=624 Hz, PH), 4.06 (m, 2H, $CH_2OP$), 3.80 (s, 6 H, $OCH_3$), 3.25 (t, 2H, $DMTOCH_2$), 3.05 (q, 6H, $N(CH_2CH_3)_3$), 1.25 (t, 9H, $N(CH_2CH3)_3$). $^{31}$P NMR ($CDCl_3$); 5.89.

EXAMPLE 3

Synthesis of 2-O-(Dimethoxytrityl)-ethylsuccinate Half Ester

A solution of 2-O-(dimethoxytrityl)ethanol (1.0 g, 2.77 mmol), triethylamine (0.4 ml, 3 mmol), and 4-dimethylamino-pyridine catalyst (120 mg, 1 mmol) in dry dichloroethane was treated with succinic anhydride (410 mg, 0.41 mmol). The mixture was stirred at 50° C. for 1.5 hr and then cooled to room temperature. The mixture was kept at room temperature for 16 hrs. The mixture is filtered and the filtrate was purified by silica gel flash column chromatography using chloroform-methanol-triethylamine to yield the title compound as a triethylammonium salt. $^1$H NMR: (CDCl$_3$) δ 7.50–7.20, 6.90–6.80 (m, 13 H, ArH), 4.26 (t, 2H, CH$_2$OCO), 3.80 (s, 6 H, OCH$_3$), 3.25 (t, 2H, DMTOCH$_2$), 3.05 (q, 6H, N(CH$_2$CH$_3$)$_3$), 2.70 (m, 4H, OOCCH$_2$CH$_2$COO), 1.25 (t, 9H, N(CH$_2$CH$_3$)$_3$.

EXAMPLE 4

Derivatization of LCAA CPG With 2-O-(Dimethoxytrityl)-ethylsuccinate Half Ester 2-O-(Dimethoxytrityl)ethylsuccinate half ester triethylammonium salt (135 mg) was dissolved in dichloromethane (5 ml). 4-Dimethylaminopyridine catalyst (40 mg, 0.2 mmol) was added followed by toluene diisocyanate (0.029 ml, 0.2 mmol). The mixture was shaken for 18 min. Long chain alkyl amine controlled pore glass (LCAA CPG) (1.0 g) was added and the mixture was shaken with the exclusion of light for 16 hrs. The mixture was filtered and washed with dichloromethane and then diethylether (3×10 ml each). The CPG was shaken for 16 hrs in pyridine/water (4:1), filtered, and rinsed with pyridine (5×5 ml). A 10 mg sample of the dried CPG was treated with 3% trichloroacetic acid in dichloromethane. The presence of the trityl ion qualitatively verified the derivatization. The loading was measured to be 30 µmol/g by measuring the absorbance of the dimethoxytrityl cation.

EXAMPLE 5

Oligomer Synthesis via Sequential Coupling of 2-O-(Dimethoxytrityl)ethoxy-phosphonic Acid to the Derivatized CPG of Example 4

The dimethoxytrityl protecting group of the derivatized resin in Example 4 is removed by a treatment with 2% dichloroacetic acid followed by washing with dry acetonitrile. The resin is then washed with acetonitrile-pyridine (4:1) followed by a simultaneous treatment of the CPG with 20–30 equivalents of 2-O-(dimethoxytrityl)ethoxy-phosphonic acid and 20–30 equivalents of adamantane carbonyl chloride in acetonitrile-pyridine. The mixture is agitated by circulating the reagents in the synthesis vessel for 10–15 minutes. The CPG is then briefly washed with acetonitrile-pyridine and then treated with diisopropyl phosphite adamantane carbonyl chloride to cap all unreacted hydroxyl groups. Finally, the CPG is washed with acetonitrile-pyridine and then acetonitrile. An estimate of coupling efficiency is derived from the treatment of the oligomer with dichloracetic acid in acetonitrile followed by a measurement of the absorbance of an aliquot at 498 nm.

The CPG is treated with 2% dichloroacetic acid in acetonitrile and washed with dry acetonitrile. The CPG is then washed with acetonitrile-pyridine (4:1) followed by a simultaneous treatment of the CPG with 20–30 equivalents of the 2-O-(dimethoxytrityl)ethoxy-phosphonic acid and 20–30 equivalents of adamantane carbonyl chloride in acetonitrile-pyridine. The mixture is agitated by circulating the reagents in the synthesis vessel for 10–15 minutes. The CPG is then briefly washed with acetonitrile-pyridine and then treated with diisopropyl phosphite adamantane carbonyl chloride. Lastly, the CPG is washed with acetonitrile-pyridine and then acetonitrile to yield the derivatized CPG. An estimate of the second coupling may be made as above. Repeating the above procedure n times will yield an oligomer with n+1 backbone segments and n H-phosphonate linkages which is tethered to a LCAA resin by a succinate group as described above.

EXAMPLE 6

Synthesis of 10-O-(Dimethoxytrityl)-1-decanol

A solution of decane-1,10-diol in dry pyridine and containing excess triethylamine is treated with one equivalent of dimethoxytrityl chloride for a period of six hours. The resulting solution is evaporated to dryness under reduced pressure, the residue redissolved in methylene chloride and the solution washed with cold saturated sodium bicarbonate, water and brine. The organic phase is separated, dried over sodium sulfate, filtered and again evaporated under reduced pressure. The resulting residue is flash-chromatographed on silica gel using ethyl acetate-hexanes to isolate the purified product. Characterization by H-NMR yields signals for the DMT group (multiplet, 8.0–7.0 ppm), the decane group (multiplets, 1.2–4.0 ppm) and the alcohol (variable).

EXAMPLE 7

Synthesis of 10-O-(Dimethoxytrityl)decyloxy-phosphonic acid

A solution of three equivalents of imidazole in dry acetonitrile is treated dropwise with one equivalent of PCl3 over a period of 30 minutes. The resulting solution is further treated with excess triethylamine to drive the reaction to completion. After 1 hr the mixture is treated with a solution of one equivalent of 10-O-(dimethoxytrityl)decan-1,10-diol in dry acetonitrile and the mixture stirred at room temperature for an additional hour. This mixture is treated with an excess of a solution of triethylammonium bicarbonate, pH 8, to yield the title compound. The compound is purified by repeated extraction of the bicarbonate solution with ethyl acetate. Pooling and drying of the extracts over sodium bicarbonate followed by evaporation of the solvent under reduced pressure yields a compound which is used as such without further purification. Characterization by $^{31}$P NMR (doublet, 6 ppm, JP-H=600 Hz) and $^1$H NMR yields signals for the DMT and the decane groups as for 10-O-(dimethoxytrityl)decandiol and signals for the triethylammonium groups (doublet, triplet, 3.2–2.2 ppm).

EXAMPLE 8

Synthesis of 10-O-(Dimethoxytrityl)decylsuccinate Half Ester

A solution of 10-O-(dimethoxytrityl)decan-1,10-diol in dry dichloromethane is treated with one equivalent of succinic anhydride, excess triethylamine and 5 mole % of 4-dimethylaminopyridine catalyst. The mixture is stirred overnight under anhydrous conditions and then further diluted with dichloromethane. This solution is washed with cold, saturated sodium bicarbonate, water and brine. The solution is then dried over magnesium sulfate, filtered and evaporated to dryness under reduced pressure. The resulting solid is purified by silica gel flash column chromatography using ethyl acetate-methanol-triethylamine to yield the title compound as the triethylammonium salt. The free acid is obtained by repeated coevaporation of this material with wet methanol. Characterization by $^1$H NMR yields signals for the DMT and decylene groups as for 10-O-(dimethoxytrityl) decan-1,10-diol and signals for the succinic group (two closely spaced doublet of doublets, 2.5–3.0 ppm).

EXAMPLE 9

Derivatization of LCAA CPG with 10-O-(Dimethoxytrityl)decyl-succinate Half Ester A commercially obtained sample of controlled pore glass derivatized with long chain alkylamine groups (LCAA CPG) is suspended in dry acetonitrile. In a separate dry container, 10-O-(dimethoxytrityl)decylsuccinate half ester is treated with two equivalents of pentafluorophenol, excess triethylamine and two equivalents of dicyclohexyl carbodiimide. The mixture containing activated 10-O-(dimethoxytrityl) decylsuccinate half ester is stirred under argon for one hour and then added to the suspension of CPG while maintaining anhydrous conditions. The mixture is then shaken gently for 6 hr, the supernatant is separated and the process is repeated twice more. The quantity of 10-O-(dimethoxytrityl) decylsuccinate half ester which is used in each treatment is based on the concentration of available amine groups per gram of LCAA CPG, generally found to be 25–40 mmoles/ gram. The CPG is then treated with a dilute solution of acetic anhydride in pyridine for 1 hr to cap all unreacted amine functionalities and then washed several times with acetonitrile. The extent to which this CPG has been derivatized is determined by treating an accurately weighed sample of the resulting CPG with 2% dichloroacetic acid in acetonitrile and measuring the absorbance of an aliquot of the supernatant at 498 nm.

EXAMPLE 10

Oligomer Synthesis Via Sequential Coupling of 10-O-(dimethoxytrityl)decyl-phosphonic Acid to Derivatized CPG The dimethoxytrityl group of the derivatized CPG from Example 9 is removed by a treatment with 2% dichloroacetic acid followed by washing with dry acetonitrile. The CPG is washed with acetonitrile-pyridine (1:1) followed by a simultaneous treatment of the CPG with 10 to 30 equivalents of the 10-O-(dimethoxytrityl)decyl-phosphonic acid as the triethylammonium salt, 20–30 equivalents of adamantane carbonyl chloride in acetonitrile-pyridine. The CPG is then washed with acetonitrile-pyridine and then treated with diisopropyl phosphite adamantane carbonyl chloride (0.2M) to cap all unreacted hydroxyl groups. Finally, the CPG is washed with acetonitrile/pyridine 1:1 and then acetonitrile. An estimate of coupling efficiency is derived from the treatment of the CPG with dichloracetic acid in acetonitrile followed by a measurement of the absorbance of an aliquot at 498 nm. Repeating the above procedure n times will yield an oligomer with n+1 decane units and n H-phosphonate linkages. The oligomer is tethered to a LCAA CPG by a succinate group as described above.

EXAMPLE 11

(N1-Thymine)-2-Acetic Acid

Methyl bromoacetate (25.5 g, 15.2 ml, 160 mmol) was added to a suspension of $K_2CO_3$ (44.2 g, 320 mmol) and thymine (20.2 g, 160 mmol) in 500 ml dry DMF with stirring overnight. The suspension was filtered and the solvent removed under reduced pressure. The residue was suspended in 120 ml $H_2O$ and 30 ml 4N HCl, stirred for 30 minutes and filtered again. The solid was suspended in 250 ml $H_2O$, to which was added 100 ml 2.5M NaOH. The solution was heated to boiling, cooled and acidified to pH 1 with concentrated HCl. The precipitate was dried in vacuo to give 13.6 g (73.6 mmol, 46%) pure product. $^1$H NMR: (DMSO-d6, 200 MHz) δ 7.48 (s, 1H, H6), 4.37 (s, 2H, $CH_2$), 1.76 (s, 3H, $CH_3$).

EXAMPLE 12

N-4-Benzoyl-1-cytosine-2-acetic acid

Cytosine hemihydrate (12.0 g, 100 mmol) was coevaporated with pyridine and resuspended in 250 ml dry pyridine. Benzoyl chloride (58 ml, 70.3 g, 500 mmol) was added dropwise (exothermic). The solution was stirred at RT overnight, and water (50 ml) carefully added. The solvent was evaporated, and the residue dissolved in 700 ml $H_2O$ containing 55 g NaOH. The solution was stirred for 1 h after complete dissolution of the material. Concentrated HCl was then added to pH 4.0, the white precipitate was collected and boiled in 1 liter EtOH, cooled to RT and filtered to give 16.1 g product (75%).

To a suspension of N-4-Benzoylcytosine (15.0 g, 69.7 mmol) and $K_2CO_3$ (9.7 g, 70 mmol) in 500 ml DMF was added methyl bromoacetate (6.6 ml, 10.7 g, 70 mmol). The suspension was stirred vigorously for 3 days, filtered and evaporated. The residue was treated with water (120 ml), and 10 ml 4N HCl for 15 min, and the solid collected by filtration. The residue was resuspended in 120 ml water, and 60 ml 2N NaOH added. The suspension was stirred at RT for 45 min, until all the solids had dissolved. The solution was acidified to pH 2 with conc HCl, filtered, and the solid dried in vacuo at 60° C. to give 11.6 g product (61%).

EXAMPLE 13

(N6-Benzoyl-9-Adenine)-2-Acetic Acid

Sodium hydride (8.20 g 60% in oil, 205 mmol) was added to a suspension of adenine (25.0 g, 185 mmol) in 500 ml DMF. After vigorous stirring for 2 hours using a mechanical stirrer, $H_2$ evolution stopped and a thick slurry was obtained. Ethyl bromoacetate (55.6 g, 36.9 ml, 333 mmol) was added dropwise over 3 hours, and stirring continued for a further 1 hour. Water (10 ml) and $H_2SO_4$ were added to pH 4. The solvent was evaporated and the residue suspended in 500 ml $H_2O$, filtered and washed with water. The residue was recrystallized from 400 ml ethanol to give 23.8 g (108 mmol, 58%) pure product.

To a suspension of (9-adenylyl)-2-acetic acid ethyl ester (6.06 g, 27.4 mmol) in 250 ml dry pyridine was added benzoyl chloride (9.60 ml, 11.6 g, 82 mmol), and the solution stirred for 4 hours at room temperature. Methanol (25 ml) was added and the solvents evaporated. The residue was dissolved in ethyl acetate (2×250 ml), washed with 0.1N HCl, $H_2O$, saturated $NaHCO_3$, brine, and dried with $Na_2SO_4$. The organic extracts were evaporated and the solid residue was redissolved in 250 ml THF at 0° C., to which was added 100 ml 1M NaOH. The solution was stirred at 0° C. for 1 hour and acidified to pH 1 with concentrated HCl, and the aqueous portion extracted once with ether. The product, which began to crystallize almost immediately, was collected by filtration to yield 4.96 g (61%). $^1$H NMR: (DMSO-d6, 200 MHz) δ8.86, 8.84 (d, H2, HS), 8.1 (d, 2H, J=7.0 Hz, ArH), 7.69–7.58 (m, 3H, Ar-H), 5.22 (s, 2H, $CH_2$).

EXAMPLE 14

N-2-Isobutyroyl-9-Guanylyl-2-Acetic Acid

To a suspension of 2-amino-6-chloropurine (10 mmol) and $K_2CO_3$ (15 mmol) in DMF (25 ml) is added ethyl bromoacetate (10 mmol). The mixture is stirred vigorously for 24 hrs, filtered and the solvent evaporated. The residue is resuspended in 25 ml pyridine and isobutyroyl chloride added (20 mmol). After stirring for 18 hrs, water is added and the solvent removed. The residue is suspended in 1N HCl and heated to reflux for 1 hr. The suspension is then cooled to 0° C., NaOH added to pH 12, and the suspension stirred for 1 hr. The solution is acidified to pH 3, and the product is collected by filtration.

EXAMPLE 15

2-N-Fmoc-2-Amino-1,3-Propanediol

2-Aminol-1,3-propandiol (3.48 g, 38.2 mmol) and NaHCO$_3$ (8.00 g, 95.2 mmol) are suspended in 150 ml HaO/Dioxane (1:1). Fluorenylmethyl chloroformate (11.4 g, 44.0 mmol) in 25 ml toluene is added dropwise. The temperature of the reaction is maintained below 25° C. during the addition. The mixture is stirred vigorously overnight, and then quenched with 50 ml saturated NaHCO$_3$ solution and 50 ml water. The solution is extracted with 100 ml diethyl ether. The aqueous layer is acidified to pH 1 with concentrated HCl, and extracted twice with ethyl acetate, and the organic extracts are washed with brine. The solution is dried with MgSO$_4$, filtered and the solvent removed in vacuo. The crude material is purified by silica gel column chromatography to give the title compound.

EXAMPLE 16

1-O-Dimethoxytrityl-N-Fmoc-2-Amino-1,3-Propanediol

A solution of N-Fmoc-2-amino-1,3-propandiol (13.79 g, 44 mmol) in dry pyridine (250 ml) is cooled to 0° C. in an ice bath. Excess triethylamine (7 ml) and 4-dimethylaminopyridine catalyst (120 mg, 1 mmol) is added followed by the slow addition of dimethoxytrityl chloride (14.8 g, 44 mmol) over 30 minutes. The mixture is stirred at 0° C. until complete. The resulting solution is quenched with methanol and evaporated to dryness under reduced pressure. The residue is dissolved in saturated NaHCO$_3$ and extracted with EtOAc. The EtOAc extracts are washed with cold saturated sodium bicarbonate and brine. The organic phase is separated, dried over sodium sulfate, filtered and evaporated under reduced pressure. The resulting residue is purified by flash column chromatography on silica gel to give the title compound.

EXAMPLE 17

1-O-Dimethoxytrityl-N-Fmoc-2-Amino-3-O-phosphonic Acid-1,3-Propanediol

A solution of imidazole (4.29 g, 63 mmol)in dry acetonitrile at 0° C. (300 ml) is treated dropwise with PCl$_3$ (1.77 ml, 20.3 mmol) over a period of 30 minutes. The resulting solution is further treated with triethylamine (9.06 ml, 65 mmol). To the thick slurry was added 1-O-dimethoxytrityl-N-Fmoc-2-amino-1,3-propanediol (3.58 g, 5.81 mmol) in anhydrous acetonitrile (150 ml) slowly over a period of 30 minutes. The mixture is allowed to warm to room temperature and stirred for 15 minutes. The mixture is quenched with pyridine/water 9:1 (100 mL) and the mixture is evaporated in vacuo to a minimum volume and extracted with dichloromethane (2×150 ml). The dichloromethane extracts are washed with water and evaporated in vacuo. The residue is purified by silica gel column chromatography using dichloromethane/MeOH/pyridine to give the title compound.

EXAMPLE 18

1-O-Dimethoxytrityl-N-Fmoc-2-Amino-1,3-Propanediol Succinate Half Ester

1-O-Dimethoxytrityl-N-Fmoc-2-amino-1,3-propanediol is treated with succinic anhydride as per the procedure of Example 3 to give the title compound.

EXAMPLE 19

Derivatization of LCAA CPG With 1-O-Dimethoxytrityl-N-Fmoc-2-Amino-1,3-Propanediol Succinate Half Ester 1-O-Dimethoxytrityl-N-Fmoc-2-amino-1,3-propanediol succinate half ester is derivatized onto LCAA CPG as per the procedure of Example 4 to give the derivatized resin.

EXAMPLE 20

1-O-Dimethoxytrityl-2-Amino-1,3-Propanediol Succinate Derivatized Resin

The Fmoc protecting group on the 2-amino group of the 1-O-dimethoxytrityl-N-Fmoc-2-amino-1,3-propanediol succinate derivatized CPG is removed by treatment with piperidine in dimethylformamide (DMF). CPG bound 1-O-dimethoxytrityl-N-Fmoc-2-amino-1,3-propanediol is treated with 2 equivalents of piperidine in DMF. The CPG is then washed with acetonitril/pyridine 1:1 and then treated a second time with 2 equivalents of piperidine in DMF. Finally, the CPG is washed with acetonitrile-pyridine and then acetonitrile to give the deprotected material.

EXAMPLE 21

1-O-Dimethoxytrityl-2-N-(acetylthymine)amino-1,3-propanediol Succinate Derivatized Resin Method A The 1-O-dimethoxytrityl-2-amino-1,3-propanediol succinate derivatized resin (2.0 g, 1.0 mmol/gm loading, 1% crosslinked) is swollen in dichloroethane (200 mL) and to this is added 1-carboxymethyl thymine (2.0 g, 10 mmol), [O-(7-azabenzotriazol-1-yl)-1,1,3,-tetramethyluronium hexafluorophosphate (3.8 g, 10 mmol) and triethylamine (2.0 g, 20 mmol). The reaction mixture is heated to 40° C. for 18 hours, then cooled and the resin is washed 5 times with dichoromethane (50 mL), then 3 times with diethyl ether (100 mL), and is dried at low vacuum at 40° C. for 18 hours. The free flowing resin powder is used as is.

Method B

The 1-O-dimethoxytrityl-2-amino-1,3-propanediol succinate derivatized resin (2.0 g, 1.0 mmol/gm loading, 1% crosslinked) is swollen in dichloroethane (200 mL) and to this is added HOBt (0.1M), PyBOP (0.1M), N-methylmorpholine (0.15M), as solutions in DMF followed by 1-carboxymethyl thymine (2.0 g, 10 mmol). coupling is allowed to proceed for 2–3 hours or overnight. The resin is washed 5 times with dichoromethane (50 mL), then 3 times with diethyl ether (100 mL), and is dried at low vacuum at 40° C. for 18 hours. The free flowing resin powder is used as is.

EXAMPLE 22

Sequential Addition and functionalization of n Backbone segments

The dimethoxytrityl protecting group of the derivatized resin is removed by a treatment with 2% dichloroacetic acid followed by washing with dry acetonitrile. The resin is then washed with acetonitrile-pyridine (4:1) followed by a simultaneous treatment of the CPG with 10 equivalents of 1-O-dimethoxytrityl-N-Fmoc-2-amino-3-O-phosphonic acid-1,3-propanediol and 30 equivalents of adamantane carbonyl chloride in acetonitrile-pyridine. The mixture is agitated by circulating the reagents in the synthesis vessel for 2 minutes. The CPG is then briefly washed with acetonitrile-pyridine and then treated with diisopropyl phosphite adamantane carbonyl chloride to cap all unreacted hydroxyl groups. The CPG is washed with acetonitrile-pyridine and then acetonitrile. The resulting phosphonic acid diester is reacted with a large molar excess of diethyl amine (the amine letter) in carbon tetrachloride/pyridine. The solid support is shaken for 15 minutes and the supernatant is removed by filtration. The solid support is washed with pyridine. A second treatment with a large molar excess of diethyl amine in carbon tetrachloride/pyridine followed by shaking will ensure efficient oxidation to the phosphoramidate. The Fmoc protecting group is removed as per the procedure of Example 20. The resulting free amine group is treated with 1-carboxymethyl thymine as per the procedure of Example 21. This procedure is repeated twice to give a 2mer having acetyl thymine groups corresponding to the letter and the tether covalently bound to the amine group attached to carbon in the backbone segment. The functional groups bound to the phosphoramidate nitrogen are ethyl groups. This procedure when repeated n times will give a fully functionalized oligomer that is n+1 backbone segments long.

Upon completion of the addition of the last of the desired length and configuration of oligomeric sequence, the solid support is washed with pyridine/acetonitrile and the phosphoramidate is cleaved from the resin by treatment with concentrated ammonium hydroxide at room temperature for 3 hours. Evaporation of the supernatant and purification of the phosphoramidate on an RP-18 HPLC column yields the final oligomer.

EXAMPLE 23

N-Fmoc-Aspartic Acid-β-Benzyl Ester

2-Aminoaspartic acid-β-benzyl ester (150 mmol) and diisopropylethylamine (66.3 ml, 49.1 g, 380 mmol) are suspended in 150 ml H$_2$O+300 ml dioxane. Fluorenylmethyl chloroformate (43.25 g, 1.1 eq) in 100 ml dioxane is added dropwise. The temperature of the reaction is not allowed to rise above 10° C. during the addition. The mixture is stirred vigorously overnight, and most of the solvent removed in vacuo. Water and satd bicarbonate solution are added (250 ml each), and the solution extracted with 250 ml diethyl ether, which is discarded. The aqueous layer is acidified to pH 1 with conc HCl, and extracted twice with ethyl acetate (2×300 ml), and the organic extracts washed with brine. The solution is dried with MgSO$_4$, filtered and the solvent removed in vacuo to give the title compound.

EXAMPLE 24

4-Hydroxy-2-N-Fmoc-aminobutanoic acid

2-N-Fmoc-aminoaspartic acid-β-benzyl ester (10 mmol) is dissolved in dry THF (100 ml), cooled to 0° C. and Lithium borohydride (15 mmol) added. The solution is stirred at 0° C. and then room temperature until the complete disappearance of the starting material. Excess ethyl acetate is then added, and the solution is washed with 0.1M citric acid solution, brine and dried with MgSO$_4$. The crude material is purified by flash chromatography to give the title compound.

EXAMPLE 25

4-O-Dimethoxytrityl-2-N-Fmoc-aminobutanoic acid

4-Hydroxy-2-N-Fmoc-aminobutanoic acid (30 mmol) is coevaporated with dry pyridine (2×50 ml), redissolved in 200 ml dry pyridine, and cooled in an ice bath. Dimethoxytrityl chloride (22.0 g, 65 mmol) is added in portions over 30 min, and the solution stirred at RT overnight. Water is then added (10 ml), and the solution stirred until the trityl ester is completely hydrolyzed. The solvent is removed under reduced pressure. The residue is dissolved in CH$_2$Cl$_2$ (300 ml), washed with 150 ml 0.1M citric acid solution, 150 ml sat NaHCO$_3$, brine, and dried with MgSO$_4$ followed by evaporation. The residue is purified by flash chromatography.

EXAMPLE 26

4-O-Dimethoxytrityl-2-N-Fmoc-aminobutan-1-ol

To a stirred solution of 4-O-Dimethoxytrityl-2-N-Fmoc-aminobutanoic acid (140 mmol) in 500 ml THF is added Borane-methyl sulfide (290 mmol, 21.8 g, 27.3 ml) dropwise at RT. Stirring is continued until the reaction is complete. Methanol is carefully added (vigorous H$_2$ evolution), and the resulting solution stirred for a further 15 min. The solvent is evaporated under reduced pressure, and the residual gum coevaporated with 2×300 ml MeOH. The product is purified by flash chromatography.

EXAMPLE 27

1-O-Dimethoxytrityl-2-N-Fmoc-2-Amino-4-Phosphonic Acid-1,4-Butanediol

1-O-Dimethoxytrityl-2-N-Fmoc-2-aminobutan-1-ol is treated as per the procedure of Example 17 to give the title compound.

EXAMPLE 28

1-O-Dimethoxytrityl-2-N-Fmoc-2-Aminobutan-1-ol-Succinic Acid Half Ester

1-O-Dimethoxytrityl-2-N-Fmoc-2-aminobutan-1-ol is treated as per the procedure of Example 18 to give the title compound.

EXAMPLE 29

1-Derivatization of LCAA CPG With 1-O-Dimethoxytrityl-2-N-Fmoc-2-Amino-4-Phosphonic Acid-1,4-Butanediol-Succinic Acid Half Ester 1-O-Dimethoxytrityl-2-N-Fmoc-2-aminobutan-1-ol-succinic acid half ester is treated as per the procedure of Example 19 to give the derivatized resin.

EXAMPLE 30

1-O-Dimethoxytrityl-2-Amino-4-Phosphonic Acid-1,4-Butanediol Derivatized Resin

The derivatized resin of Example 29 is treated as per the procedure of Example 20 to remove the Fmoc protecting group giving the title compound attached to resin.

EXAMPLE 31

1-O-Dimethoxytrityl-2-(2-N-Acetylthymine)-Amino-4-Phosphonic Acid-1,4-Butanediol Derivatized Resin The derivatized resin of Example 30 is treated with N-1-thymine-2-acetic acid as per the procedure of Example 21 to give the title compound attached to resin.

EXAMPLE 32

Synthesis of a 3-mer Having the 2-Amino-1,4-Butanediol backbone segment

1-O-Dimethoxytrityl-2-(2-N-acetylthymine)-Amino-4-Phosphonic Acid-1,4-Butanediol Derivatized Resin is treated with 1-O-dimethoxytrityl-2-N-Fmoc-2-amino-4-phosphonic acid-1,4-butanediol, morpholine, and N-1-thymine acetic acid as per the procedure of Example 22 to give a 3 mer with 2-N-acetylthymine bound to the amino groups and morpholine groups as the phosphoramidate substituent.

EXAMPLE 33

4-(N-Fmoc)-Amino-Glutamic acid-γ-methyl ester

Glutamic acid-γ-methyl ester (150 mmol) and diisopropylethylamine (66.3 ml, 49.1 g, 380 mmol) are suspended in 150 ml $H_2O$+300 ml dioxane. Fluorenylmethyl chloroformate (43.25 g, 1.1 eq) in 100 ml dioxane is added dropwise. The temperature of the reaction is not allowed to rise above 10° C. during the addition. The mixture is stirred vigorously overnight, and most of the solvent removed in vacuo. Water and said bicarbonate solution are added (250 ml each), and the solution extracted with 250 ml diethyl ether, which is discarded. The aqueous layer is acidified to pH 1 with conc HCl, and extracted twice with ethyl acetate (2×300 ml), and the organic extracts washed with brine. The solution is dried with $MgSO_4$, filtered and the solvent removed in vacuo to give the title compound.

EXAMPLE 34

5-Hydroxy-4-N-Fmoc-aminopentanoic acid methyl ester

To a solution of 4-(N-Fmoc)-amino-glutamic acid-γ-methyl ester (140 mmol) in 500 ml THF is added Borane-methyl sulfide (290 mmol, 21.8 g, 27.3 ml) dropwise at RT (3 neck flask, mechanical stirrer, condenser, dropping funnel). After the evolution of $H_2$ has ceased, the solution is heated to reflux with vigorous stirring. After 1 hr a white precipitate has formed. Methanol is carefully added (vigorous $H_2$ evolution), and the resulting solution refluxed for a further 15 min. The solution is cooled to RT, the solvents evaporated under reduced pressure, and the residual gum coevaporated with 2×300 ml MeOH. The product is purified by flash chromatography.

EXAMPLE 35

5-O-Dimethoxytrityl-4-Fmoc-aminopentanoic acid methyl ester

5-Hydroxy-4-Fmoc-aminopentanoic acid methyl ester (30 mmol) is coevaporated with dry pyridine (2×50 ml), redissolved in 200 ml dry pyridine, and cooled in an ice bath. Dimethoxytrityl chloride (11.0 g, 32.5 mmol) is added in portions over 30 min, and the solution stirred at 0° C. overnight. Methanol is then added (10 ml), and the solvent removed under reduced pressure. The resulting gum is redissolved in toluene (100 ml), filtered to remove the pyridinium hydrochloride and taken to dryness again. The residue is dissolved in $CH_2Cl_2$ (300 ml), washed with 150 ml 0.1M citric acid solution, 150 ml sat $NaHCO_3$, brine, and dried with $MgSO_4$ followed by evaporation. The residue is purified by flash chromatography to give the title compound.

EXAMPLE 36

5-O-Dimethoxytrityl-4-Fmoc-aminopentan-1-ol

5-O-Dimethoxytrityl-4-Fmoc-aminopentanoic acid methyl ester (10 mmol) is dissolved in dry THF (100 ml), cooled to 0° C. and Lithium borohydride (10 mmol) added. The solution is stirred at 0° C. and then room temperature until the complete disappearance of the starting material. Excess ethyl acetate is then added, and the solution washed with 0.1M citric acid solution, sat $NaHCO_3$, brine and dried with $MgSO_4$. The product is purified by flash chromatography.

EXAMPLE 37

5-O-Dimethoxytrityl-4-N-Fmoc-2-aminopentan-1-ol hydrogen phosphonate

Imidazole (6.81 g, 100 mmol) is dissolved in 400 ml dry $CH_3CN$ and cooled to 0° C. Phosphorus trichloride (2.62 ml, 4.12 g, 30 mmol) is added dropwise, followed by triethylamine (21 ml, 15.2 g, 150 mmol). A thick slurry develops to which is added over 15 min a solution of 5-O-dimethoxytrityl-4-N-Fmoc-2-amino-1,5-pentanediol (10 mmol) in 50 ml $CH_3CN$. Once the addition is complete, the ice bath is removed and the solution stirred at RT for 30 min. The reaction is stopped by the addition of 100 ml pyridine/water (9:1). The solvent is removed and the residue extracted (3×200 ml) with $CH_2Cl_2$, and washed with water. The organic phase is dried with $MgSO_4$ and concentrated under reduced pressure. The product is further purified by flash chromatography using a gradient of MeOH (1–10%) in $CH_2Cl_2$+1% pyridine.

EXAMPLE 38

5-O-Dimethoxytrityl-4-N-Fmoc-2-Amino-1,5-pentanediol_Succinic Acid Half Ester

5-O-Dimethoxytrityl-4-N-Fmoc-2-amino-1,5-pentanediol is treated as per the procedure of Example 18 to give the title compound.

EXAMPLE 39

1-Derivatization of LCAA CPG With 1-O-Dimethoxytrityl-2-N-Fmoc-2-Amino-5-Phosphonic Acid-1,5-Pentanediol-Succinic Acid Half Ester 1-O-Dimethoxytrityl-2-N-Fmoc-2-amino-1,5-pentanediol-succinic acid half ester is treated as per the procedure of Example 19 to give the derivatized resin.

EXAMPLE 40

1-O-Dimethoxytrityl-2-Amino-4-Phosphonic Acid-1,5-Pentanediol Derivatized Resin

The derivatized resin of Example 28 is treated as per the procedure of Example 20 to remove the Fmoc protecting group giving the title compound attached to resin.

EXAMPLE 41

1-O-Dimethoxytrityl-2(phenylacetyl)-Amino-5-Phosphonic Acid-1,5-pentanediol Derivatized Resin The derivatized resin of Example 29 is treated with phenyl acetic acid as per the procedure of Example 21 to give the title compound attached to resin.

EXAMPLE 42

Synthesis of a 3-mer Having the 2-Amino-1,5-pentanediol backbone segment

1-O-Dimethoxytrityl-2(phenylacetyl)-Amino-5-Phosphonic Acid-1,5-pentanediol Derivatized Resin is treated with 1-O-dimethoxytrityl-2-N-Fmoc-2-amino-5-phosphonic acid-1,5-pentanediol, morpholine, and phenylacetic acid as per the procedure of Example 22 to give a 3 mer with phenylacetyl bound to the amino groups and morpholine groups as the phosphoramidate substituent.

EXAMPLE 43A

Oxidative Incorporation of Letters at H-Phosphonate Linkages For Oligomeric Compounds With Letters on The Phosphoramidate Method A: Incorporation of Letters In Predetermined Sequence The solid support (e.g. LCAA CPG) is derivatized with a first backbone segment as per the procedure of Example 4 for an ethylene backbone segment or Example 9 for a decyl backbone segment. Next, the desired phosphonic acid monoester is condensed onto the derivatized solid support as per the procedure of Examples 5 and 10. The resulting phosphonic acid diester is reacted with a large molar excess of the amine letter next in the sequence. The amine letter is added in solution in carbon tetrachloride/pyridine. For the addition of two adjacent like letters in the oligomeric structure, the oxidation step is delayed until the backbone to support all of these letters is synthesized and all H phosphonate sites that will bear this letter are then oxidized simultaneously. (To improve the efficiency of incorporation of the letters into phosphoramidates or phosphorothioamidates, a coupling agent, i.e. 1-(3-dimethylaminopropyl)-3-ethylcarbodiimide hydrochloride (EDC) or dicyclohexylcarbodiimide (DCC) or triphenylphosphine, are added.) The solid support is shaken for 15 minutes and the supernatant is removed by filtration. The solid support is washed with pyridine. A second treatment with a large molar excess of the amine letter in carbon tetrachloride/pyridine followed by shaking will ensure efficient oxidation to the phosphoramidate. The above steps are repeated until all of the letter of the oligomer have been added. All letters are predetermined in this method of synthesis. Upon completion of the addition of the last of the desired length and configuration of oligomeric sequence, the solid support is washed with pyridine/acetonitrile and the phosphoramidate is cleaved from the resin by treatment with concentrated ammonium hydroxide at room temperature for 3 hours. Evaporation of the supernatant and purification of the phosphoramidate on an RP-18 HPLC column yields the final oligomer.

Method B: Incorporation of Letters in a Random Sequence

The method of oligomer synthesis as described in Examples 5 and 10 is repeated to synthesize the oligomer of desired length. To randomize the amine letters on the oligomer, the method of adding a letter as described in Method 1 above is followed except that, for randomization, the amine letters in carbon tetrachloride and a suitable cosolvent are added as a mixture, preferably one normalized for relative reactivity. Random distribution of amine letters from this mixture of amine letters is verified experimentally by treatment of an oligomer, which has been previously treated with a mixture of amine letters and subsequently worked up and purified, with 10% aqueous formic acid at 50°–70° C. to release the amine letters. The actual percentages of incorporation of the individual amine letters is then determined by HPLC analysis of the reaction mixture and the relative individual rates are calculated. Having once determined the relative rates, in further iteration of the sequences, the concentration of amine letters within a mixture is adjusted to reflect these rate differences.

In a variation of this method of randomization, in a five mer all sites of which are to be randomized, the oxidation is effected simultaneously. The five mer backbone was synthesized as above and a mixture of the letters added. Upon completion of the backbone synthesis, the oxidation of amine letters is effected on all five sites as a single step.

In a further variation of this method of randomization, upon completion of the synthesis of the first backbone fragment, the resin is split into five portion and each portion is individual oxidized with one of the amine letter. The individual portions of the resin are recombined and the backbone is extended a further unit. The resin is then again split, and the individual portion each oxidized with one of the amine letter. This cycle is repeated to complete the synthesis.

Method C: Incorporation of Amine Letters in Fixed/random Sequence

Combining methods 1 and 2 above can be used to fix certain positions while randomizing other positions as the oligomeric structure is synthesized. This method is further used in combination with a SURF combinatorial strategy.

EXAMPLE 43B

Oxidative Incorporation of Letters at H-Phosphonothioate Linkages For Oligomeric Compounds With Letters on The Phosphorothioamidate Oxidative incorporation of letters at H-phosphonothioate linkages for compounds with letters on the phosphorothioamidate linkage is accomplished using the procedures of Example 43 with the following exceptions. A backbone segment is attached to the solid support. The protected hydroxyl group on the backbone segment is deblocked and treated with bis(diisopropylamino)chlorophosphine in the presence of triethylamine or other suitable base following the method contained in U.S. Pat. No. 5,218,103, issued Jun. 8, 1993. The resulting intermediate is reacted with a protected backbone segment followed by treatment with hydrogen sulfide to form the H phosphonothioate diester. Oxidative treatment with amine letters as per Example 22 above gives the phosphorothioamidate. Modifying Example 43 with the above procedures will enable the preparation of predetermined, random or mixed oligomeric compounds having the phosphorothioamidate linkages.

EXAMPLE 44A

Oxidative Incorporation of Letters at H-Phosphonate Linkages For Oligomeric Compounds With Letters on The Phosphoramidate and The Backbone Segment Method A: Incorporation of Letters In a Predetermined Sequence The solid support (e.g. LCAA CPG) is derivatized with a first backbone segment as per the procedure of Example 19 for a 1-O-dimethoxytrityl-N-Fmoc-2-amino-1,3-propanediol backbone. The 2-amino group is deprotected and functionalized with a letter having an optional tether as per the procedures of Examples 20 and 21. Next, the desired phosphonic acid monoester is condensed onto the derivatized solid support as per the procedure of Example 22. The resulting phosphonic acid diester is reacted with a large molar excess of the amine letter next in the sequence. The amine letter is added in solution in carbon tetrachloride/pyridine (to improve the efficiency of incorporation of the letters into phosphoramidates a coupling agent, i.e. 1-(3-dimethylaminopropyl)-3-ethylcarbodiimide hydrochloride (EDC) or dicyclohexylcarbodiimide (DCC) or triphenylphosphine for example, is added). The solid support is shaken for 15 minutes and the supernatant is removed by filtration. The solid support is washed with pyridine. A second treatment with a large molar excess of the amine letter in carbon tetrachloride/pyridine followed by shaking will ensure efficient oxidation to the phosphoramidate. The solid support is washed with pyridine and then acetonitrile. The 2-amino group of the backbone segment is deprotected and functionalized with a letter having an optional tether as per the procedures of Examples 20 and 21. The above steps are repeated until all of the letters at backbone segments and phosphoramidate sites of the oligomer have been added. All letters are predetermined in this method of synthesis. Upon completion of the addition of the last of the desired length and configuration of oligomeric sequence, the solid support is washed with pyridine/acetonitrile and the phosphoramidate is cleaved from the resin by treatment with concentrated ammonium hydroxide at room temperature for 3 hours. Evaporation of the supernatant and purification of the phosphoramidate on an RP-18 HPLC column yields the final oligomer.

Method B: Incorporation of Letters in a Random Sequence

The solid support (e.g. LCAA CPG) is derivatized with a first backbone segment as per the procedure of Example 19 for a 1-O-dimethoxytrityl-N-Fmoc-2-amino-1,3-propanediol backbone and the Fmoc protecting group is removed with an appropriate agent. The resin is split into five portions and each portion is separately functionalized at the 2-amino group with a particular letter having an optional tether as per the procedures of Examples 20 and 21. The resin is combined and the desired phosphonic acid monoester is condensed onto the derivatized solid support as per the procedure of Example 22. The resin is split into five portions and each portion is separately oxidized with one of the amine letters. The individual portions of the resin are recombined and the Fmoc groups are removed as above and the resin is again split into five portions and each portion is separately treated with one of five letters having optional tethers as per the procedures in Method 1. This cycle is repeated to complete the synthesis.

Method C: Incorporation of Amine Letters in Fixed/random Sequence

Combining methods 1 and 2 above is used to fix certain positions while randomizing other positions as the oligomeric structure is synthesized. This method is further used in combination with a SURF combinatorial strategy.

EXAMPLE 44B

Oxidative Incorporation of Letters at H-Phosphonothioate Linkages For Oligomeric Compounds With Letters on The Phosphonothioate and The Backbone Segment Oxidative incorporation of letters at H-phosphonothioate linkages for compounds with letters on the phosphorothioamidate linkage and the backbone segment is accomplished using the procedures of Example 44A with the following exceptions. A backbone segment is attached to the solid support. The protected active site is deprotected and functionalized with a letter having an optional tether as per the procedures of Examples 20 and 21. If this position is to be randomized the bead splitting of Example 44A Method B is performed. The protected hydroxyl group on the backbone segment is deblocked and treated with bis (diisopropylamino)chlorophosphine in the presence of triethylamine or other suitable base following the method contained in U.S. Pat. No. 5,218,103, issued Jun. 8, 1993. The resulting intermediate is reacted with a protected backbone segment followed by treatment with hydrogen sulfide to form the H phosphonothioate diester. Oxidative treatment with amine letters as per Example 44A (Methods A, B or C) above gives the phosphorothioamidate. Modifying Example 44A with the above procedures will enable the preparation of predetermined, random or mixed oligomeric compounds having the phosphorothioamidate linkages.

EXAMPLE 45

Benzylamine Phosphoramidate Oligomer Synthesis

A solid support is derivatized with 2-O-(dimethoxytrityl) ethylsuccinate half ester as in Example 4. 2-O-(dimethoxytrityl)ethyl-phosphonic acid is condensed onto the derivatized resin as in Example 5. The above method of example 5 is repeated until six of the above phosphonic acid residues are incorporated. The resulting six mer is treated using the procedure of Example 22, Method 1, with a large excess of benzylamine in carbon tetrachloride/pyridine. The solid support is shaken for 15 minutes and the supernatant is removed by filtration and then washed with pyridine. A second treatment with a large excess of benzylamine in carbon tetrachloride/pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hr. Evaporation of the supernatant and purification of the phosphoramidate on an RP-18 HPLC column will yield the final oligomer. The stepwise M phosphonate coupling efficiency is determined by measuring the absorbance of the trityl ion as described in Example 9.

EXAMPLE 46

Random Letter Phosphoramidate Oligomer Synthesis

The resin is derivatized with 2-O-(dimethoxytrityl) ethylsuccinate half ester as in Example 4, 2-O-(dimethoxytrityl)ethyl-phosphonic acid is condensed with the derivatized resin as in Example 5. The above method of Example 5 is repeated until six of the above phosphonic acid residues have been incorporated. The resulting six mer is treated as per the procedure of Example 43A, Method B, with a large excess of an equal molar mixture of benzylamine, 2-(2-aminoethyl)-1-methylpyrrolidine, and piperonyl amine in carbon tetrachloride/pyridine. The resin is shaken for 15 minutes and the supernatant is removed by filtration and then washed with pyridine. A second treatment with a large excess of the mixture of amine letters in carbon tetrachloride/pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hr. Evaporation of the supernatant and purification of the phosphoramidates on an RP-18 HPLC column will yield the final random oligomers. The stepwise H phosphonate coupling efficiency will be determined by measuring the absorbance of the trityl ion as previously described above.

EXAMPLE 47

Random Letter(s)/fixed Letter(s) Phosphoramidate Oligomer Synthesis

The resin is derivatized with 2-O-(dimethoxytrityl) ethylsuccinate half ester as in Example 4, 2-O-(dimethoxytrityl)ethyl-phosphonic acid is condensed with the derivatized resin as in Example 5. The above method of example 5 is repeated until 3 of the above phosphonic acid residues have been incorporated. The resulting trimer is treated as illustrated in Example 43A, Method B, with a large excess of a mixture of benzylamine, 2-(2-aminoethyl)-1-methylpyrrolidine, and piperonyl amine in carbon tetrachloride/pyridine. The resin is detritylated with trichloroacetic acid. The resin is treated with 2-O-(dimethoxytrityl) ethyl-phosphonic acid as in Example 5 and further treated as per the procedure of Example 43, Method A with benzylamine to fix position 4 in the growing oligomer. The resin is washed with pyridine/acetonitrile and then the phosphoramidate is cleaved from the resin by a treatment with concentrated ammonium hydroxide at room temperature for 3 hr. Evaporation of the supernatant and purification of the phosphoramidates on an RP-18 HPLC column yields the final random/fixed oligomers. The coupling efficiency is determined by measuring the absorbance of the trityl ion as described in Example 9.

EXAMPLE 48

Phosphoramidate Oligomeric Compounds With Fixed or Fixed/random Letters and Further Containing Asymmetric Tether Lengths Ethylene glycol is protected with dimethoxytrityl chloride as per the procedure of Example 1 and further reacted with succinic anhydride as per the procedure of Example 3. The resulting 2-O-(dimethoxytrityl)ethylsuccinate half ester is activated and derivatized onto LCAA CPG as per the procedure Example 4. 1,3-propanediol is protected with dimethoxytrityl chloride as per the procedure of Example 1 and further reacted with $PCl_3$ as per the procedure of Example 2 to give 3-O-(dimethoxytrityl)propyl-phosphonic acid. The 3-O-(dimethoxytrityl)propyl-phosphonic acid is reacted with the 2-O-(dimethoxytrityl)ethylsuccinate derivatized LCAA CPG as per the procedure of Example 5 to give 3-O-(dimethoxytrityl)propoxy-[(2-O-succinyl-LCAA-CPG)-ethoxy]-H phosphonate.

The 3-O-(dimethoxytrityl)propoxy-[(2-O-succinyl-LCAA-CPG)-ethoxy]-H phosphonate is then treated with N-butylamine as per the procedure of Example 43A (except that the compound is kept attached to the resin) to give 3-O-(dimethoxytrityl)propoxy-[(2-O-succinyl-LCAA-CPG)-ethoxy]-N-butyl-phosphoramidate. 1,4-butanediol is protected with dimethoxytrityl chloride as per the procedure of Example 1 and further reacted with $PCl_3$ as per the procedure of Example 2 to give 4-O-(dimethoxytrityl)butyl-phosphonic acid. 3-O-(dimethoxytrityl)propoxy-[(2-O-succinyl-LCAA-CPG)-ethoxy]-N-butyl-phosphoramidate is detritylated and further reacted with the 4-O-(dimethoxytrityl)butyl-phosphonic acid as per the procedure of Example 5 and further treated with N-propylamine as per the procedure of example 43A. The resulting dimer is cleaved off the solid support using the procedure of Example 43A, and purified by HPLC. The resulting oligomeric dimer is substituted at the two phosphoramidate nitrogens by N-butane and N-propane going from left to right. The phosphoramidate units are separated by a propane backbone segment and flanked on the left by an ethyl backbone segment and on the right by a butyl backbone segment. Substitution of a mixture of N-butylamine and N-propylamine for the N-propylamine above gives a two mer substituted with N-butane at position one and a random substitution of both N-butane and N-propane at position two.

EXAMPLE 49

Bis(diisopropylamino)phosphine-2-O-ethylsuccinyl-LCAA-CPG

2-O-(Dimethoxytrityl)ethylsuccinate half ester derivatized solid support from Example 4, is detritylated using standard methods (e.g. 3% trichloroacetic acid) and further treated with bis(diisopropylamino) chlorophosphine as per Example III of U.S. Pat. No. 5,218,103 dated Jun. 8, 1993 to form the solid support bound diamidite.

EXAMPLE 50

2-O-Dimethoxytritylethoxy-Bis(diisopropylamino) phosphine-2-O-ethylsuccinyl-LCAA-CPG The bis(diisopropylamino)phosphine-2-O-ethylsuccinyl-LCAA-CPG from Example 24 is then treated with 2-O-(dimethoxytrityl)ethanol from Example 1, as per the procedure of Example III of U.S. Pat. No. 5,218,103 to give the title compound.

EXAMPLE 51

2-O-Dimethoxytritylethoxy-hydrogenphosphonothioate-2-O-ethyl-succinyl-LCAA-CPG 2-O-Dimethoxytritylethoxy-bis(diisopropylamino) phosphine-2-O-ethylsuccinyl-LCAA-CPG from Example 25 is treated with hydrogen sulfide and tetrazole as per the procedure of Example III of U.S. Pat. No. 5,218,103 to give the title compound.

EXAMPLE 52

2-O-Dimethoxytritylethoxy-N-butylphosphorothioamidate-2-O-ethylsuccinyl-LCAA-CPG 2-O-Dimethoxytritylethoxy-hydrogenphosphonothioate-2-O-ethylsuccinyl-LCAA-CPG from Example 26 is oxidized with $I_2$ in the presence of a selected amine letter, e.g N-butyl amine, utilizing the procedure of Example VI of U.S. Pat. No. 5,218,103 to give the title compound.

EXAMPLE 53

Oxidative Incorporation of Letters to Hydrogenphosphonothioates (Random Sequences of Letters) General Methods Ethylene glycol is protected with dimethoxytrityl chloride as per Example 1 and further reacted with succinic anhydride as per Example 3. The resulting 2-O-(dimethoxytrityl) ethylsuccinate half ester is activated and derivatized onto LCAA CPG as per Example 4. Further treatment with bis(diisopropylamino)chlorophosphine as per the procedure of Example 16 gives the solid support bound ethoxy-bis (diisopropylamino)-phosphine. The solid support bound ethoxy-bis(diisopropylamino)-phosphine is reacted with 3-O-(dimethoxytrityl)propanol prepared as per the procedure of Example 1 to give 3-O-(dimethoxytrityl)propoxy-[(2-O-succinyl-LCAA-CPG)-ethoxy]-diisopropylaminophosphoramidite. The 3-O-(dimethoxytrityl)propoxy-[(2-O-succinyl-LCAA-CPG)-ethoxy]-diisopropylaminophosphoramidite is treated with hydrogen sulfide as per the procedure of Example 43B to give 3-O-(dimethoxytrityl)-propoxy-[(2-O-succinyl-LCAA-CPG)-ethoxy]-diisopropylamino H phosphonothioate.

The 3-O-(dimethoxytrityl)propoxy-[(2-O-succinyl-LCAA-CPG)-ethoxy]-diisopropylamino H phosphonothioate is treated with an equal molar mixture of N-butylamine and N-propylamine as per the procedure of Example 43A to give 3-O-(dimethoxytrityl)propoxy/butoxy-[(2-O-succinyl-LCAA-CPG)-ethoxy]-N-(N-butyl)-phosphorothioamidate. 1,4-butanediol is protected with dimethoxytrityl chloride as per the procedure of Example 1 and further reacted with bis(diisopropylamino)-chlorophosphine as per the procedure of example 43B to give 4-O-(dimethoxytrityl)(butoxy-bis(diisopropylamino)-phosphine. The 3-O-(dimethoxytrityl)propoxy-[(2-O-succinyl-LCAA-CPG)-ethoxy]-N-(N-butyl)-phosphorothioamidate is detritylated as per the procedure of Example 5 and further reacted with the 4-O-(dimethoxytrityl)butoxy-bis(diisopropylamino)-phosphine. Treatment with hydrogen sulfide as per the procedure of Example 43B gives the monosubstituted dimer. Treatment of the monosubstituted dimer with an equal molar mixture of N-butylamine and N-propylamine as per the procedure of Example 43A gives the disubstituted/randomized two met. This is treated as per the procedure of Example 20 to cleave the oligomeric compound off the solid support. It is further purified by HPLC. The resulting oligomeric dimer is substituted at the two phosphorothioamidate nitrogens by N-butane and N-propane in an equal molar random distribution.

EXAMPLE 54

Phosphorothioamidate Oligomeric Compounds With Fixed or Fixed/random Letters and Containing Symmetric Tether Lengths Ethylene glycol is protected with dimethoxytrityl chloride as per Example 1 and further reacted with succinic anhydride as per Example 3. The resulting 2-O-(dimethoxytrityl) ethylsuccinate half ester is activated and derivatized onto LCAA CPG as per Example 4. Further treatment with bis(diisopropylamino)chlorophosphine as per the procedure of Example 43B gives the solid support bound ethoxy-bis (diisopropylamino)-phosphine. The solid support bound ethoxy-bis(diisopropylamino)-phosphine is reacted with 3-O-(dimethoxytrityl)propanol prepared as per the procedure of Example 1 to give 3-O-(dimethoxytrityl)propoxy-[(2-O-seconal-LCAA-CPG)-ethoxy]-diisopropylaminophosphoramidite. The 3-O-(dimethoxytrityl)propoxy-[(2-O-succinyl-LCAA-CPG)-ethoxy]-diisopropylaminophosphoramidite is treated with hydrogen sulfide as per the procedure of Example 43B to give 3-O-(dimethoxytrityl)propoxy-[(2-O-seconal-LCAA-CPG)-ethoxy]-diisopropylamino H phosphonothioate.

The 3-O-(dimethoxytrityl)propoxy-[(2-O-succinyl-LCAA-CPG)-ethoxy]-diisopropylamino H phosphonothioate is treated with N-butylamine as per the procedure of Example 43A to give 3-O-(dimethoxytrityl)propoxy-[(2-O-seconal-LCAA-CPG)-ethoxy]-N-(N-butyl)-phosphorothioamidate. 1,4-butanediol is protected with dimethoxytrityl chloride as per the procedure of Example 1 and further reacted with bis(diisopropylamino) chlorophosphine as per the procedure of example 43B to give 4-O-(dimethoxytrityl)butoxy-bis(diisopropylamino)-phosphine. The 3-O-(dimethoxytrityl)propoxy-[(2-O-succinyl-LCAA-CPG)-ethoxy]-N-(N-butyl)-phosphorothioamidate is detritylated as per the procedure of Example 5 and further reacted with the 4-O-(dimethoxytrityl)butoxy-bis(diisopropylamino)-phosphine. Treatment with hydrogen sulfide as per the procedure of Example 43B gives the monosubstituted 2-mer.

Treatment of the monosubstituted two mer with N-butylamine as per the procedure of Example 43A gives the disubstituted 2-mer. Utilizing the procedure of Example 43A, the oligomeric compound is cleaved off the solid support and purified by HPLC. The resulting oligomeric two mer is substituted at the two phosphorothioamidate nitrogens by N-butane and N-propane going from left to right. The phosphoramidate units are separated by a propane backbone segment and flanked on the left by an ethyl backbone segment and on the right by a butyl backbone segment. Substitution of a mixture of N-butylamine and N-propylamine for the N-propylamine above gives a two mer substituted with N-butane at position one and a random substitution of both N-butane and N-propane at position two.

EXAMPLE 55

Chimeric Oligomeric Structure

A fifteen-merphosphorothioate-phosphoramidate-phosphorothioate chimeric compound is synthesized on an automated DNA synthesizer (Applied Biosystems model 380B) utilizing commercially available oligonucleotide reagents and compounds of the invention using standard phosphoramidite and phosphorothioate chemistries (see, Oligonucleotide Synthesis, A Practical Approach, M. J. Gait., ed., Oxford University Press, New York, 1990). The chimeric compound is synthesized in a standard 3 prime to 5 prime direction (e.g. 3 prime attached to solid support). The stepwise thiation of the phosphite linkage, to generate the phosphorothioate portion of the oligomer, is achieved utilizing a 0.2M solution of 3H-1,2,-benzodithiole-3-one 1,1-dioxide in acetonitrile. A five mer oligonucleotide phosphorothioate is synthesized using standard solid phase chemistry to give the oligonucleotide sequence TTTTT attached to a solid support. The five mer is further reacted with 2-O-dimethoxytrityl-ethyl-phosphonic acid (Example 2) as per the procedure of Example 5. The resulting H phosphonate is in the six position is oxidized with benzyl amine as per the procedure of Example 43. Positions 7 thru 10 are similarly substituted in a step wise manner by coupling with 2-O-dimethoxytrityl-ethyl-phosphonic acid followed by oxidation in the presence of benzylamine. The dimethoxytrityl group of the terminal backbone segment attached to the terminal phosphoramidate is removed using standard methods as in Example 5 and the remaining 5 nucleotides are incorporated using standard methods as above. Cleaving the fifteen mer off the solid support and deprotection of the DMT group in position 15 gives the fifteen mer.

EXAMPLE 56

PLA$_2$ Assay

The oligomer libraries are screened for inhibition of PLA$_2$ in an assay using *E. coli* labeled with $^3$H-oleic acid (see, Franson, et al., *J. Lipid Res.* 1974, 15, 380; and Davidson, et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each the oligomeric pools is done in water: 10 μl of each oligomer is incubated for 5 minutes at room temperature with a mixture of 10 μl $PLA_2$, 20 μl 5X $PLA_2$ Buffer (500 mM Tris 7.0–7.5, 5 mM $CaCl_2$), and 50 μl water. Each of the oligomer samples is run in duplicate. At this point, 10 μl of $^3H$ *E. coli* cells is added. This mixture is incubated at 37° C. for 15 minutes.

The enzymatic reaction is stopped with the addition of 50 μl 2M HCL and 50 μl fatty-acid-free BSA (20 mg/ml PBS), vortexed for 5 seconds, and centrifuged at high speed for 5 minutes. 165 μl of each superhate is then put into a scintillation vial containing 6 ml of scintillant (ScintiVerse) and cpms are measured in a Beckman Liquid Scintillation Counter. As a control, a reaction without oligomer is run alongside the other reactions as well as a baseline reaction containing no oligo as well as no $PLA_2$ enzyme. CPMs are corrected for by subtracting the baseline from each reaction data point.

EXAMPLE 57

Verification Of Assay

The $PLA_2$ test system of Example 56 was verified using phosphorothioate oligonucleotides with one or more strings of guanosine nucleotides (at least 3 per string). Libraries of these oligonucleotides were deconvoluted using the SURF screening strategy and were shown to have an inhibitory effect on the $PLA_2$ enzyme. Knowing that phosphorothioate oligonucleotides inhibit $PLA_2$ with some sequence specificity, an eight nucleotide phosphorothioate library consisting of the four natural bases was used to test the assay system for suitability as a SURF screen. This library had been synthesized for use in another system and all subsets were not still available (indicated by dashes in Table III, below). Using the SURF method, it was confirmed that a stretch of guanosines were necessary for inhibition of $PLA_2$ activity by the phosphorothioate oligonucleotide (Table III, below).

TABLE III

Inhibition of $PLA_2$ Activity by Library Subsets $IC_{50}$ (mM)

| X = A | X = G | X = CX = T |
|---|---|---|
| Round 2 | | |
| NNGNXNNN | >50 | <u>25</u> > 50 > 50 |
| Round 3 | | |
| NNGXGNNN | — | <u>10</u> > 50 — |
| Round 4 | | |
| NNGGGXNN | 9 | <u>46</u>18 |
| Round 5 | | |
| NAGGGGXN | 4 | <u>2</u>44 |
| NGGGGGXN | 2.5 | <u>2</u>33 |
| NCGGGGXN | 5 | <u>4</u>55 |
| NTGGGGXN | 19 | <u>5</u>1715 |

The assay was sensitive and accurate enough to discriminate between subsets of oligomers so that an inhibitory sequence could be selected. In each of the first three rounds of selection, the most active subset was readily determined.

After 5 rounds, there was little difference in the activity of the subsets with at least 5 G's in a row, suggesting that the terminal positions are not critical for the inhibitory activity. The $IC_{50}$ of the "winner" improves (enzyme activity decreases) as more of the positions are fixed. As a test of the reproducibility of the assay, an eight nucleotide phosphorothioate oligonucleotide of a single sequence (TTGGGGTT) was assayed with each round of testing. This oligonucleotide acted as an internal control of the accuracy of the assay; the $IC_{50}$ was 8 μM in each assay.

EXAMPLE 58

Assay of Library of Phosphoramidate and Phosphorothioamidate Oligomeric Compounds Against $PLA_2$ A first library containing phosphoramidate oligomeric compounds and a second library containing phosphorothioamidate oligomeric compounds is tested in the $PLA_2$ assay for identification of inhibitors of type II $PLA_2$. Confirmation of the "winners" is made to confirm that the oligomers binds to enzyme rather than substrate and that the inhibition of any oligomer selected is specific for type II $PLA_2$. An assay using $^{14}C$-phosphatidyl ethanolamine ($^{14}C$-PE) as substrate, rather than *E. coli* membrane, is used to insure enzyme rather than substrate specificity. Micelles of $^{14}C$-PE and deoxycholate are incubated with the enzyme and oligomer.

$^{14}C$-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

EXAMPLE 59

Hybridization probe for the detection of specific mRNA in biological sample For the reliable, rapid, simultaneous quantification of multiple varieties of mRNA in a biological sample without the need to purify the mRNA from other cellular components, a mRNA of interest from a suitable biological sample, i.e., mRNA of a blood borne virus, a bacterial pathogen product in stool, urine and other like biological samples, is identified using standard microbiological techniques. An oligomeric compound of the invention having "nucleobase" functional groups (adenine, guanine, thymine and cytosine) complementary to the nucleic acid sequence of this mRNA is prepared as per the above examples. The oligomeric compound is immobilized on insoluble CPG solid support utilizing the procedure of Pon, R. T., Protocols for Oligonucleotides and Analogs, Agrawal, S., Ed., Humana Press, Totowa, N.J., 1993, p 465–496.

A known aliquot of the biological sample under investigation is incubated with the insoluble CPG support having the oligomer thereon for a time sufficient to hybridize the mRNA to oligomer and thus to link the mRNA via the oligomer to the solid support. This immobilizes mRNA present in the sample to the CPG support. Other non-immobilized materials and components are then washed off the CPG with a wash media suitable for use with the biological sample. The mRNA on the support is labelled with ethidium bromide, biotin or a commercial radionucleotide and the amount of label immobilized on the CPG is measured to indicate the amount of mRNA present in the biological sample.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound of the structure:

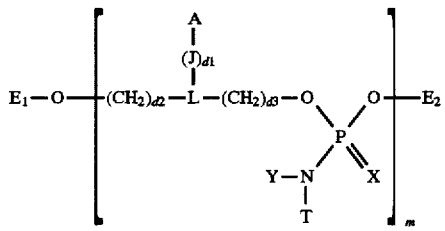

wherein
each X, independently, is O or S;
each Y, is $[Q_2]_j$—$Z_2$;
each T, independently, is $[Q_1]_k$—$Z_1$, or together Y and T are joined in a nitrogen heterocycle;
$Q_1$, $Q_2$, and each L, independently, are $C_2$-$C_{10}$ alkyl, $C_2$-$C_{10}$ alkenyl, $C_2$-$C_{10}$ alkynyl, $C_4$-$C_7$ carbocycloalkyl or -alkenyl, a heterocycle, an ether having 2 to 10 carbon atoms and 1 to 4 oxygen or sulfur atoms, a polyalkylene glycol, or $C_7$-$C_{14}$ aralkyl, provided that when L is a heterocycle, that at least one L is not a substituted pyrrolidine or a native nucleobase, and that when L is alkyl, that at least one L is not a substituted glycol;
$E_1$ and $E_2$, independently, are H, a hydroxyl protecting group, an activated solid support, a conjugate group, a reporter group, a polyethylene glycol, alkyl, oligonucleotide, peptide nucleic acid, a phosphate, a phosphite, an activated phosphate, or an activated phosphite;
j and k independently are 0 or 1;
m is 2 to about 50;
$Z_1$ and $Z_2$, independently, are H, $C_1$-$C_2$ alkyl, $C_2$-$C_{20}$ alkenyl, $C_2$-$C_{20}$ alkynyl, $C_6$-$C_{14}$ aryl, $C_7$-$C_{15}$ aralkyl, a halogen, CH=O, $OR_1$, $SR_2$, $NR_3R_4$, C(=NH)$NR_3R_4$, CH($NR_3R_4$), NHC(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;
A is $L_1$, $L_1$-$G_1$, $L_2$, $L_2$-$G_2$, $NR_3R_4$, H, a nitrogen-containing heterocycle, a purine, a pyrimidine, a phosphate group, a polyether group, or a polyethylene glycol group;
J is $L_1$, $G_3$, $L_1$-$G_3$ or $G_3$-$L_1$-$G_3$;
$L_1$ is alkyl having 1 to about 20 carbon atoms, alkenyl having 2 to about 20 carbon atoms, or alkynyl having 2 to about 20 carbon atoms;
$L_2$ is aryl having 6 to about 14 carbon atoms or aralkyl having 7 to about 15 carbon atoms;
$G_1$ is halogen, $OR_1$, $SR_2$, $NR_3R_4$, C(=NH)$NR_3R_4$, NHC(=NH)$NR_3R_4$, CH=O, C(=O)$OR_5$, CH($NR_3R_4$)(C(=O)$OR_5$), C(=O)$NR_3R_4$, a metal coordination group, or a phosphate group;
$G_2$ is halogen, OH, SH, $SCH_3$, or $NR_3R_4$;
$G_3$ is C(=O), C(=S), C(O)—O, C(O)—NH, C(S)—O, C(S)—NH or S(O)$_2$;
each d1, independently, is 0 or 1;
each d2, independently, is from 0 to 6;
each d3, independently, is from 1 to 6;
$R_1$ is H, alkyl having 1 to about 6 carbon atoms, or a hydroxyl protecting group;
$R_2$ is H, alkyl having 1 to about 6 carbon atoms, or a thiol protecting group;
$R_3$ and $R_4$ are, independently, H, alkyl having 1 to about 6 carbon atoms, or an amine protecting group; and
$R_5$ is H, alkyl having 1 to about 6 carbon atoms, or an acid protecting group.

2. The compound of claim 1 wherein L is alkyl having from about 2 to about 10 carbons.

3. The compound of claim 1 wherein together Y and T are joined in a nitrogen heterocycle.

4. The compound of claim 1 wherein $E_1$ is H, a hydroxyl protecting group, or an activated solid support.

5. The compound of claim 1 wherein $E_2$ is trityl, methoxytrityl, dimethoxytrityl or trimethoxytrityl.

6. The compound of claim 1 wherein $E_2$ is H or a hydroxyl protecting group.

7. The compound of claim 1 wherein $Z_2$ is H.

8. The compound of claim 1 wherein $Z_1$ is a purine or a pyrimidine.

9. The compound of claim 1 wherein $Z_1$ is alkyl having 1 to about 20 carbon atoms.

10. The compound of claim 1 wherein $Z_1$ is aryl having 6 to about 14 carbon atoms or aralkyl having 7 to about 15 carbon atoms.

11. The compound of claim 1 wherein $Z_1$ is fluorenylmethyl, phenyl, or benzyl.

12. The compound of claim 1 wherein $Z_1$ is polyethylene glycol or glutamyl.

13. The compound of claim 1 wherein m is from about 2 to about 25.

14. The compound of claim 1 wherein X is O.

15. The compound of claim 1 wherein X is S.

16. The compound of claim 1 wherein said

groups are of a predetermined sequence.

17. The compound of claim 1 wherein said

groups are of a random sequence.

18. The compound of claim 1 wherein at least one of said L groups is different from other of said L groups.

19. The compound of claim 3 wherein said heterocycle is piperidine or pyrrolidine.

20. The compound of claim 8 wherein $Z_1$ is adenine, guanine, cytosine, uridine or thymine.

21. A chimeric oligomeric compound having a first region comprising a phosphodiester or phosphorothioate oligonucleotide and a second region having the structure:

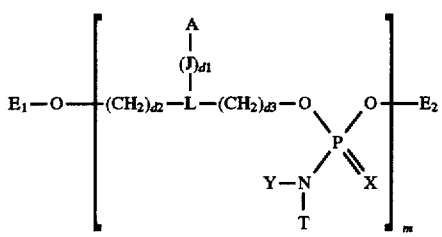

wherein:

each X, independently, is O or S;

each Y, is $[Q_2]_j$—$Z_2$;

each T, independently, is $[Q_1]_k$—$Z_1$, or together Y and T are joined in a nitrogen heterocycle;

$Q_1$, $Q_2$, and each L, independently, are $C_2$-$C_{10}$ alkyl, $C_2$-$C_{10}$ alkenyl, $C_2$-$C_{10}$ alkynyl, $C_4$-$C_7$ carbocyloalkyl or alkenyl, a heterocycle, an ether having 2 to 10 carbon atoms and 1 to 4 oxygen or sulfur atoms, a polyalkylene glycol, or $C_7$-$C_{14}$ aralkyl, provided that when L is a heterocycle, that at least one L is not a substituted pyrrolidine or a native nucleobase, and that when L is alkyl, that at least one L is not a substituted glycol;

One of $E_1$ and $E_2$ is said first region comprising a phosphodiester or phosphorothioate oligonucleotide and the other of said $E_1$ and $E_2$ is H, a hydroxyl protecting group, an activated solid support, a conjugate group, a reporter group, a polyethylene glycol, alkyl, an oligonucleotide, a peptide nucleic acid, a phosphate, a phosphite, an activated phosphate, or an activated phosphite;

j and k independently are 0 or 1;

m is 2 to about 50;

$Z_1$ and $Z_2$, independently, are H, $C_1$-$C_2$ alkyl, $C_2$-$C_{20}$ alkenyl, $C_2$-$C_{20}$ alkynyl, $C_6$-$C_{14}$ aryl, $C_7$-$C_{15}$ aralkyl, a halogen, CH=O, $OR_1$, $SR_2$, $NR_3R_4$, C(=NH)$NR_3R_4$, CH($NR_3R_4$), NHC(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;

A is $L_1$, $L_1$-$G_1$, $L_2$, $L_2$-$G_2$, $NR_3R_4$, H, a nitrogen-containing heterocycle, a purine, a pyrimidine, a phosphate group, a polyether group, or a polyethylene glycol group;

J is $L_1$, $G_3$, $L_1$-$G_3$ or $G_3$-$L_1$-$G_3$;

$L_1$ is alkyl having 1 to about 20 carbon atoms, alkenyl having 2 to about 20 carbon atoms, or alkynyl having 2 to about 20 carbon atoms;

$L_2$ is aryl having 6 to about 14 carbon atoms or aralkyl having 7 to about 15 carbon atoms;

$G_1$ is halogen, $OR_1$, $SR_2$, $NR_3R_4$, C(=NH)$NR_3R_4$, NHC(=NH)$NR_3R_4$, CH=O, C(=O)$OR_5$, CH($NR_3R_4$)(C(=O)$OR_5$), C(=O)$NR_3R_4$, a metal coordination group, or a phosphate group;

$G_2$ is halogen, OH, SH, $SCH_3$, or $NR_3R_4$;

$G_3$ is C(=O), C(=S), C(O)—O, C(O)—NH, C(S)—O, C(S)—NH or S(O)$_2$;

each d1, independently, is 0 or 1;

each d2, independently, is from 0 to 6;

each d3, independently, is from 1 to 6;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group;

$R_5$ is H, alkyl having 1 to about 6 carbon atoms, or an acid protecting group; and where one of $E_1$ and $E_2$ comprises said phosphodiester or phosphorothioate oligonucleotide and the other of said $E_1$ and $E_2$ is H, a hydroxyl protecting group or a conjugate group.

22. The compound of claim 21 wherein L is alkyl having from about 2 to about 10 carbons.

23. The compound of claim 21 wherein together Y and T are joined in a nitrogen heterocycle.

24. The compound of claim 21 wherein $E_1$ is H, a hydroxyl protecting group, or an activated solid support.

25. The compound of claim 21 wherein $E_2$ is trityl, methoxytrityl, dimethoxytrityl or trimethoxytrityl.

26. The compound of claim 21 wherein $E_2$ is H or a hydroxyl protecting group.

27. The compound of claim 21 wherein $Z_2$ is H.

28. The compound of claim 21 wherein $Z_1$ is a purine or a pyrimidine.

29. The compound of claim 21 wherein $Z_1$ is alkyl having 1 to about 20 carbon atoms.

30. The compound of claim 21 wherein $Z_1$ is aryl having 6 to about 14 carbon atoms or aralkyl having 7 to about 15 carbon atoms.

31. The compound of claim 21 wherein $Z_1$ is fluorenylmethyl, phenyl, or benzyl.

32. The compound of claim 21 wherein $Z_1$ is polyethylene glycol or glutamyl.

33. The compound of claim 21 wherein m is from about 2 to about 25.

34. The compound of claim 21 wherein X is O.

35. The compound of claim 21 wherein X is S.

36. The compound of claim 21 wherein said

groups are of a predetermined sequence.

37. The compound of claim 21 wherein said

groups are of a predetermined sequence.

38. The compound of claim 21 wherein at least one of said L groups is different from other of said L groups.

39. The compound of claim 23 wherein said heterocycle is piperidine or pyrrolidine.

40. The compound of claim 28 wherein $Z_1$ is adenine, guanine, cytosine, uridine or thymine.

* * * * *

UNITED STATES PATENT AND TRADEMARK OFFICE
CERTIFICATE OF CORRECTION

PATENT NO. : 5,717,083
DATED : February 10, 1998
INVENTOR(S) : Cook et al.

It is certified that error appears in the above-identified patent and that said Letters Patent is hereby corrected as shown below:

Column 6, line 49, please delete "necessary" and insert therefor --necessarily--.
Column 11, line 44, please delete "Satin" and insert therefor --Sarin--.
Column 11, line 61, please delete "phosphate" and insert therefor --H phosphonate"--.
Column 22, line 58, please delete "(m,13H,ARE)" and insert therefor --(m,13H, ArH)--.
Column 27, line 15, please delete "HaO/Dioxane (1:1)" and insert therefor --H2O/Dioxane (1:1)--.
Column 28, line 56, please delete "coupling" and insert therefor --Coupling--.
Column 36, line 43, please delete "M" and insert therefor --H--.
Column 39, line 37, please delete "met" and insert therefor --mer--.
Column 41, line 15, please delete "superhate" and insert therefor --supernate--.

Signed and Sealed this

Fifteenth Day of May, 2001

Attest:

NICHOLAS P. GODICI

Attesting Officer

Acting Director of the United States Patent and Trademark Office